United States Patent [19]
Roederer et al.

[11] Patent Number: 5,968,755
[45] Date of Patent: Oct. 19, 1999

[54] METHODS FOR DETERMINING T-CELL PROFILES OF IMMUNOCOMPROMISED SUBJECTS

[75] Inventors: Mario Roederer, Redwood City, Calif.; Ronald Rabin, Rockville, Md.; Leonard A. Herzenberg; Leonore A. Herzenberg, both of Stanford, Calif.

[73] Assignee: The Board of Trustees of the Leland Stanford Junior University, Stanford, Calif.

[21] Appl. No.: 08/721,260

[22] Filed: Sep. 26, 1996

Related U.S. Application Data

[60] Provisional application No. 60/004,364, Sep. 27, 1995.

[51] Int. Cl.$^6$ ..................................................... G01N 33/53
[52] U.S. Cl. ............................................. 435/7.24; 435/7.1
[58] Field of Search .............................. 435/5, 7.1, 7.24; 530/387.1

[56] References Cited

U.S. PATENT DOCUMENTS 4,918,164  4/1990  Hellstom et al. .
5,427,781  6/1995  DeFreitas et al. ...................... 424/851

OTHER PUBLICATIONS

Akbar, A.N., et al., "Inhibition of Alloresponsive Naive and Memory T Cells by cd7 and cd25 Antibodies and by Cyclosporin," Database Biosis on STN, No. BA91:31396, abstract (1990).

Andrus, L., et al., "Inhibition of T Cell Activity by Cyclosporin A," Database Biosis on STN, No. BA75:10810, abstract (1982).

Borkowsky, W., et al., "Evolution of Phenotypic Memory T Cells in HIV–1 Infected Infants and Children," *Clin. Immunol. and Immunopathol.* 63(3):280–284 (1992).

Degelau, J.J., et al., "Relationship of Memory and Naive T Cell Subsets to Diminished Influenza Vaccination Response in Nursing Home Elderly," Database Biosis on STN, No. 97449484, abstract (1994).

Froebel, K.S., et al., "Increased Expression of the CD45RO (Memory) Antigen on T Cells in HIV–Infected Children," *AIDS* 5:97–99 (1991).

Giorgi, J.V., and Detels, R., "T–Cell Subset Alternations in HIV–Infected Homosexual Men: NIAID Multicenter AIDS Cohort Study," *Clin. Immunol. and Immunopathol.* 52:10–18 (1989).

Gruters, R.A., et al., "Immunological and Virological Markers in Individuals Progressing from Seroconversion to AIDS," *AIDS* 5:837–844 (1991).

Picker, L.J., et al., "Control of Lymphocyte Recirculation in Man. I. Differential Regulation of the Peripheral Lymph Node Homing Receptor L–Selectin on T Cells During the Virgin to Memory Cell Transition," *J. Immunol.* 150(3):1105–1121 (1993).

Picker, L.J., et al., "Control of Lymphocyte Recirculation in Man. I. Differential Regulation of the Cutaneous Lymphocyte–Associated Antigen, a Tissue–Selective Homing Receptor for Skin–Homing T Cells," *J. Immunol.* 150(3):1122–1136 (1993).

Prince, H.E., et al., "Interrelationships Between Serologic Markers of Immune Activation and T Lymphocyte Subsets in HIV Infection," *J. Acquire Immune Def. Syndromes* 3:525–530 (1990).

Rabin, R.L., et al., "Altered Representation of Naive and Memory CD8 T Cell Subsets in HIV–Infected Children," *J. Clin. Invest.* 95:2054–2060 (1990).

Reddy, M.M., and Grieco, M.H., "Quantitive Changes in T Helper Inducer ($CD4^+$ $CD45RA^-$), T Suppressor Inducer ($CD4^+$ $CD45RA^+$), T Suppressor ($CD8^+$ $CD11b^+$), and T Cytotoxic ($CD8^+$ $CD11b^-$) Subsets in Human Immunodeficiency Virus Infection," *J. Clin. Lab. Anal.* 5:96–100 (1991).

Roederer, M., "T–Cell Dynamics of Immunodeficiency," *Nature Med.* 1(7):621–622 (1995).

Roederer, M., et al., "CD8 Naive T Cell Counts Decrease Profressively in HIV–Infected Adults," *J. Clin. Invest.* 95:2061–2066 (1995).

Ryan, Q.C., et al., "Maintenance of Normal T Lymphocyte Function after Transfection with SV40 Large T," *Cellular Immunol.* 149:65–81 (1993).

Teitel, J.M., et al., "Two–Year Evaluation of Clinical and laboratory Variables of Immune Function in 117 Hemophiliacs Seropositive or Seronegative for HIV–1," *Am. J. Hematol.* 32:262–272 (1989).

Ueki, Y., et al., "Lymphocyte Subsets in Hemodialysis Patients Treated with Recombinant Human Erythropoietin," Database Biosis on STN, No. BA96:103724, abstract (1993).

Jaleco, A.C., et al., "Distinct Alterations in the Distribution of CD45RO+ T–Cell Subsets in HIV–2 Compared with HIV–1 Infection," *AIDS* 8(12):1663–1668 (1994).

Gruters, R.A., et al., "Selective Loss of T Cell Functions in Different Stages of HIV Infection," *Eur. J. Immunol.* 20(5):1039–1044 (1990).

Ibegbu, C., et al., "Subpopulations of T and B Cells in Perinatally HIV–Infected and Noninfected Age–Matched Children Compared with Those in Adults," *Clin. Immunol. Immunopathol.* 71(1):27–32 (1994).

(List continued on next page.)

*Primary Examiner*—Sheela Huff
*Attorney, Agent, or Firm*—Charles K. Sholtz; Joanne R. Petithory; Peter J. Dehlinger

[57] ABSTRACT

A method of identifying an abnormal T-cell profile of an immunocompromised subject is disclosed. The method involves detecting the immunoreactivity of T-cells with at least two antibodies selectively reactive with naive T-cell surface proteins and comparing data from cells isolated from an immunocompromised subject with data from cells isolated form a non-immunocompromised subject. Also disclosed are methods of screening drugs or compounds for efficacy to stimulate the production of naive T cells in a subject.

11 Claims, 11 Drawing Sheets

OTHER PUBLICATIONS

Meyaard, L., et al., "Quantitative Analysis of CD4+ T Cell Function in the Course of Human Immunodeficiency Virus Infection," *J. Clin. Invest.* 94(5):1947–1952 (1994).

Molina, J.–M., et al., "Quantification of HIV–1 Virus Load Under Zidovudine Therapy in Patents with Symptomatic HIV Infection: Relation to Disease Progression," *AIDS* 8:27–33 (1994).

Pinto, L., et al., "Loss of CD45RA and Gain of CD45RO After In Vitro Activation of Lymphocytes from HIV–Infected Patients," *Immunology* 73(2):147–150 (1991). Cell Plaeger–Marshall, S., et al., "Activation and Differentiation Antigens on T Cells of Health, At–Risk, and HIV–Infected Children," *J. Acquir. Immune Defic. Syndr.* 6(9):984–993 (1993).

Prince, H.E., and Jensen, E.R., "Three–Color Cytofluormetric Analysis of CD8 Cell Subsets in HIV–1 Infection," *J. Acquir. Immune Defic. Snydr.* 4(12):1227–1232 (1991).

Reimann, K.A., et al., "Immunopathogenic Events in Acute Infection of Rhesus Monkeys with Simian Immunodeficiency Virus of Macaques," *J. Virol.* 68(4):2362–2370 (1994).

Sanders, M.E., et al., "Human Naive and Memory T Cells," *Immunol. Today* 9:195–199 (1988).

Sanders, M.E., et al., "Human Memory T Lymphocytes Express Increased Levels of Three Cell Adhesion Molecules (LFA–3, CD2, and LFA–1) and Three Other Molecules (UCHL1, CDw29, and Pgp–1) and Have Enhanced IFN–$\tau$ Production," *J. Immunol.* 140:1401–1407 (1988).

Watret, K.C., et al., "Phenotype Characterization of $CD8^+$ T Cell Populations in HIV Disease and in Anti–HIV Immunity," *Clin. Exp. Immunol.* 92(1):93–99 (1993).

Rabin, R.L et al. May 1995. J. Clin. Invest. 95:2054–2060.

Roederer, M et al. May 1995. J. Clin. Invest 95:2061–2066.

Ibegbu, C. et al. 1994. Clin. Immunol. Immunopathol. 71(1):27–31.

Mobley, JL. et al. 1994. J. Immunol. 153(12):5443–5452.

Bommhardt, U. et al. 1991, Eur. J. Immunol. 24:2974–2981.

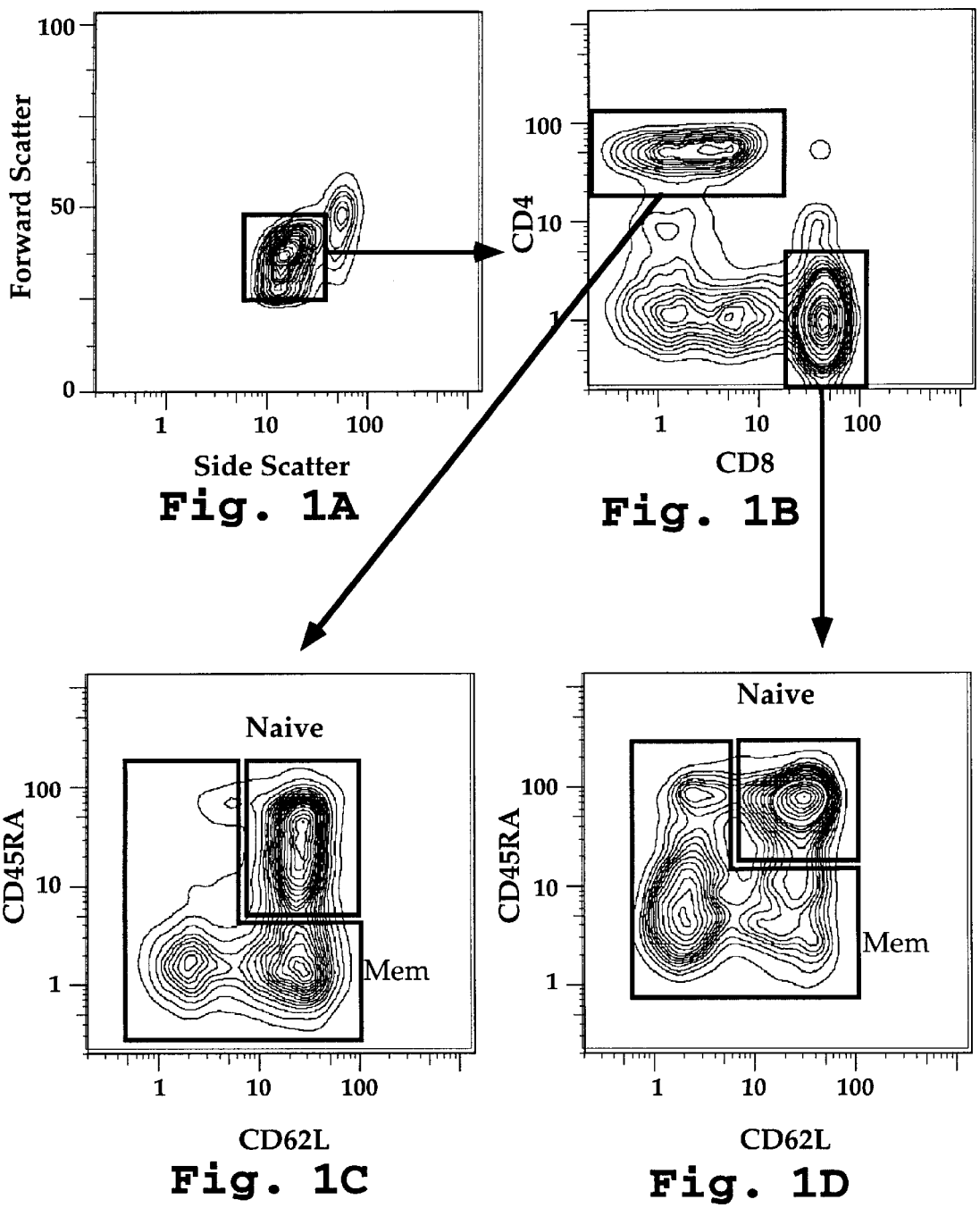

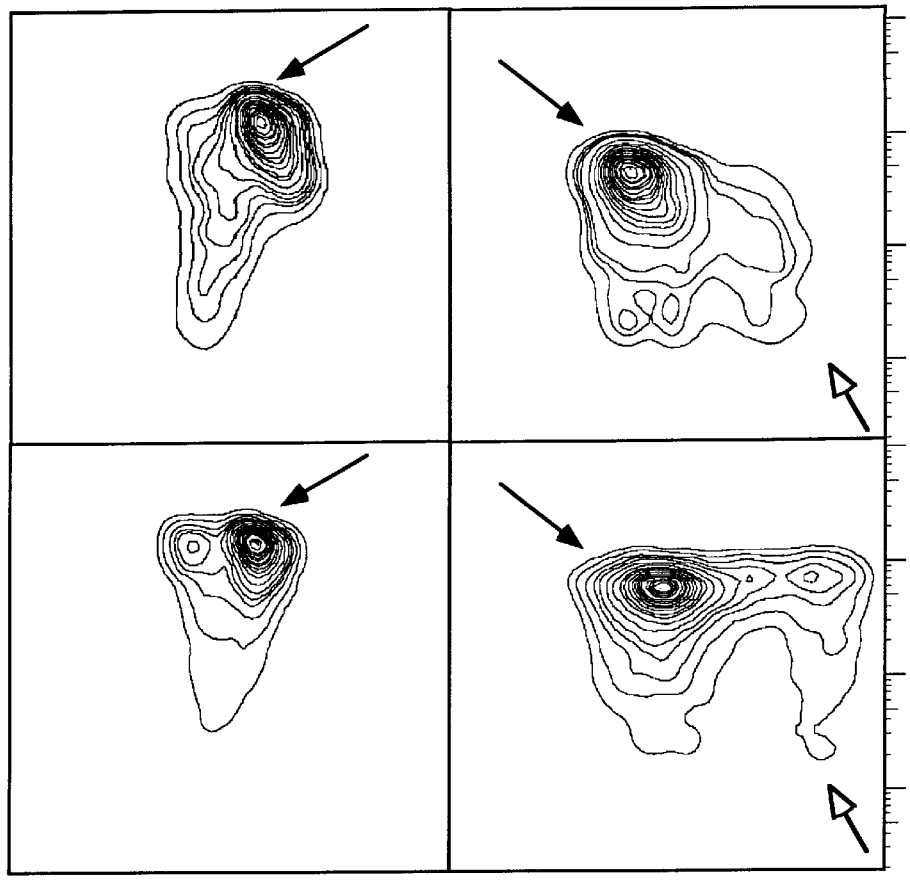

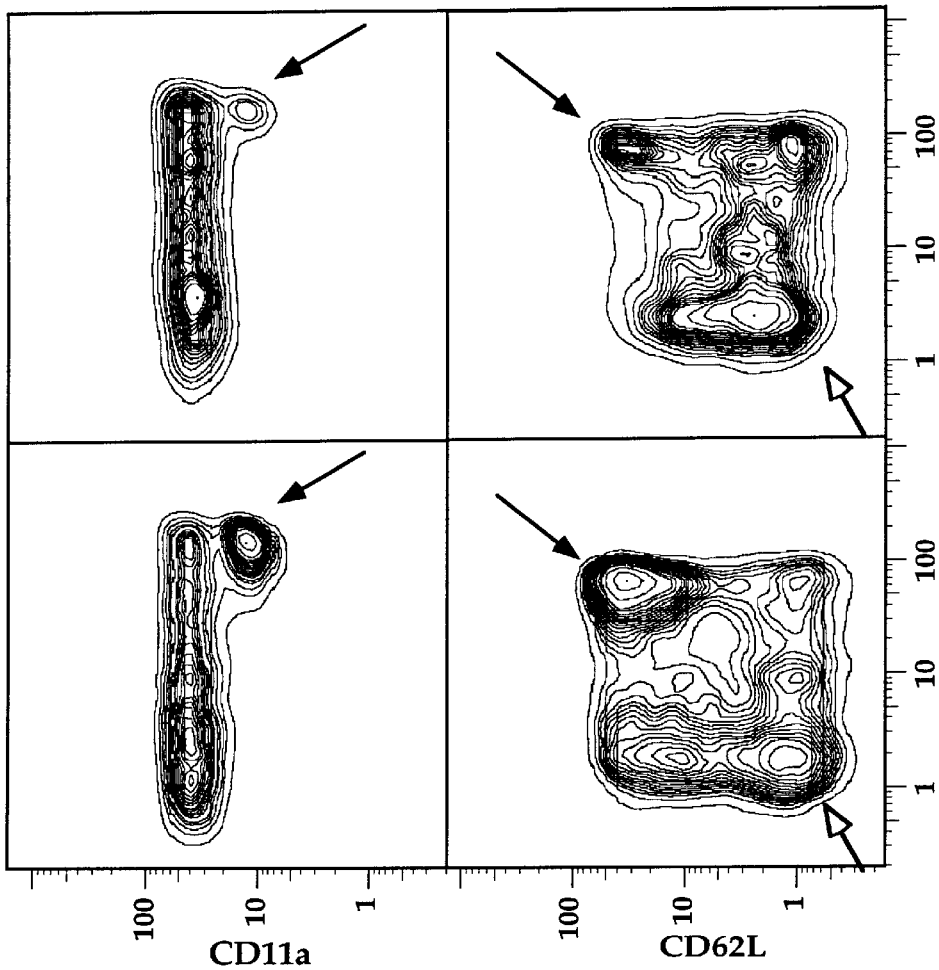

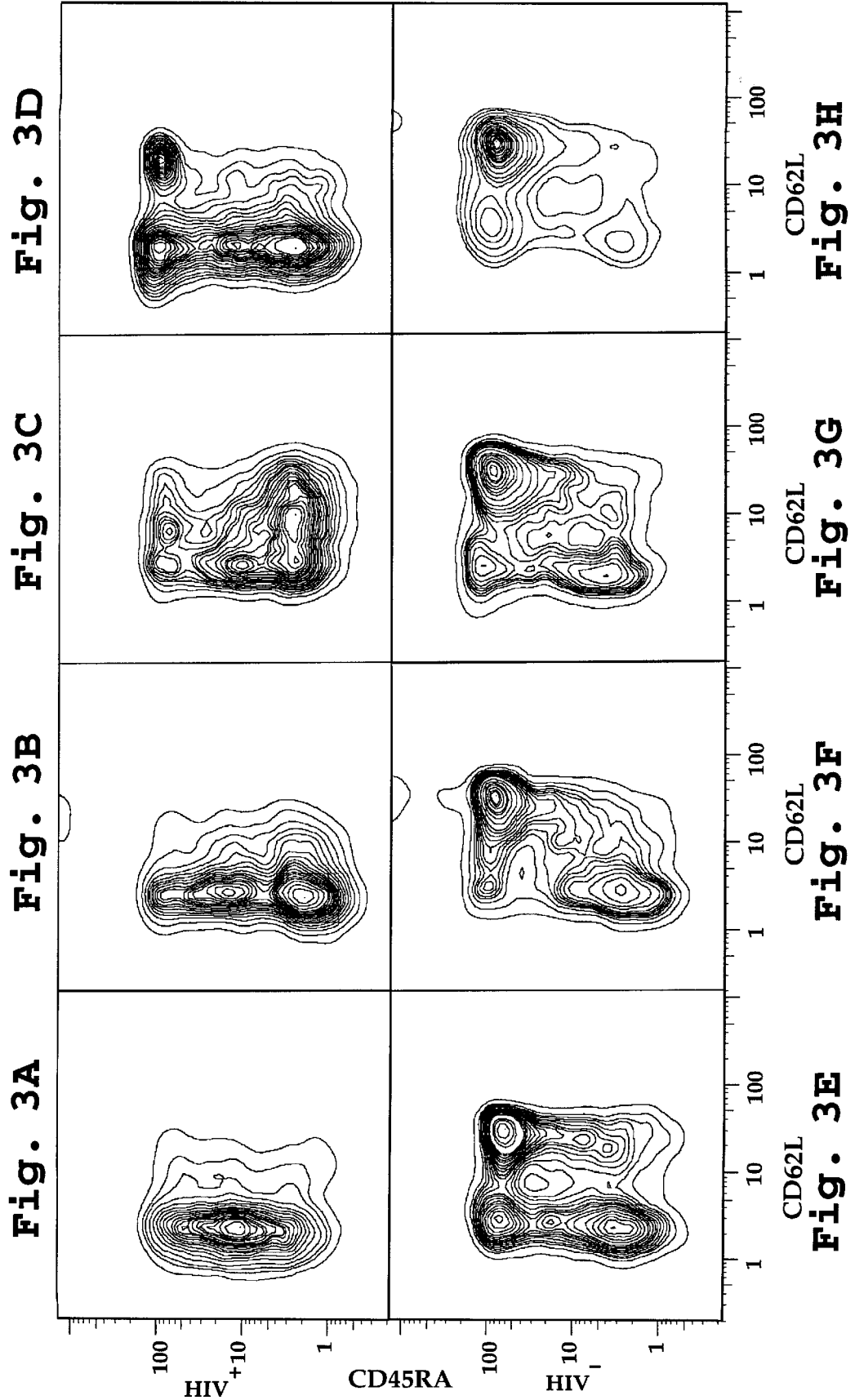

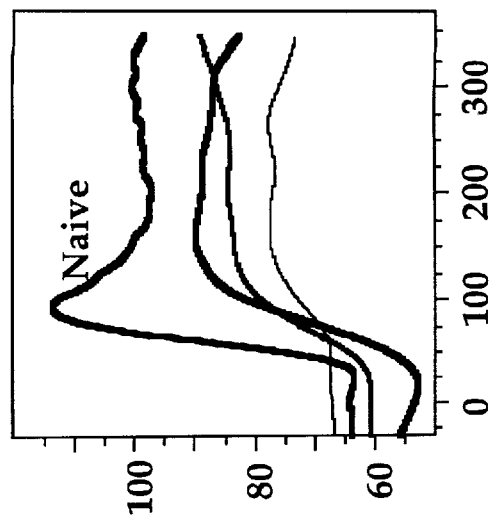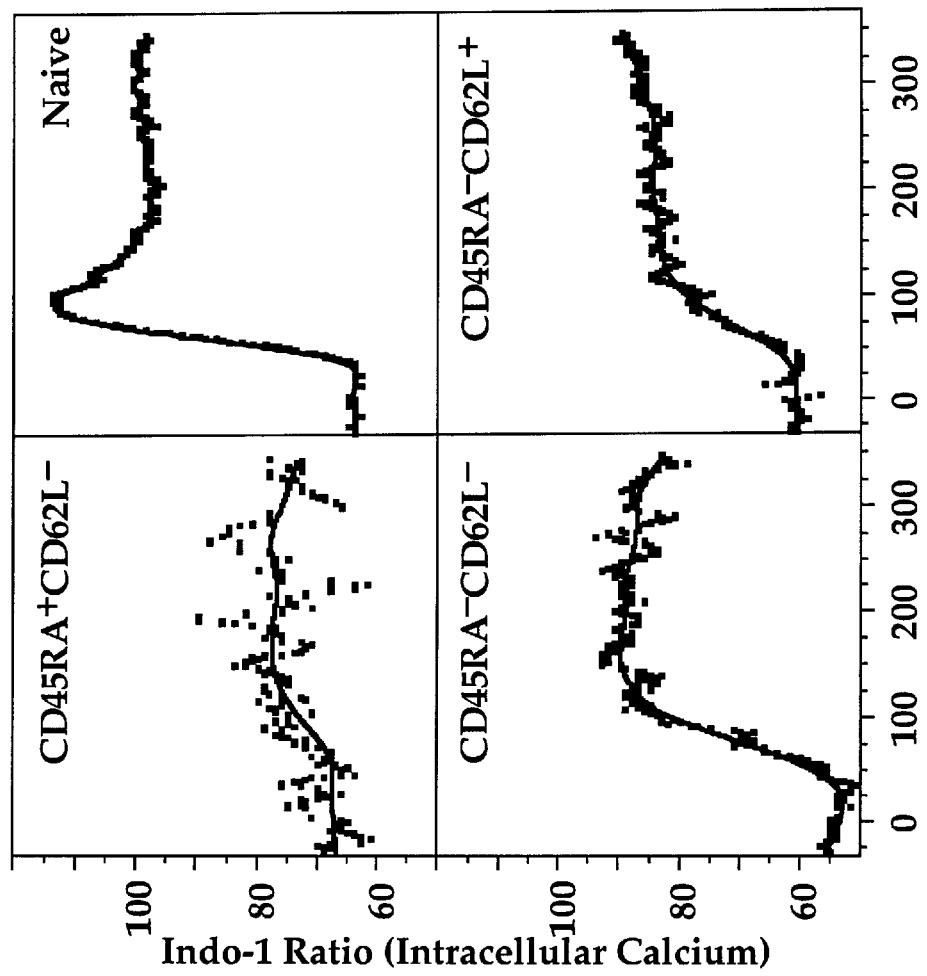

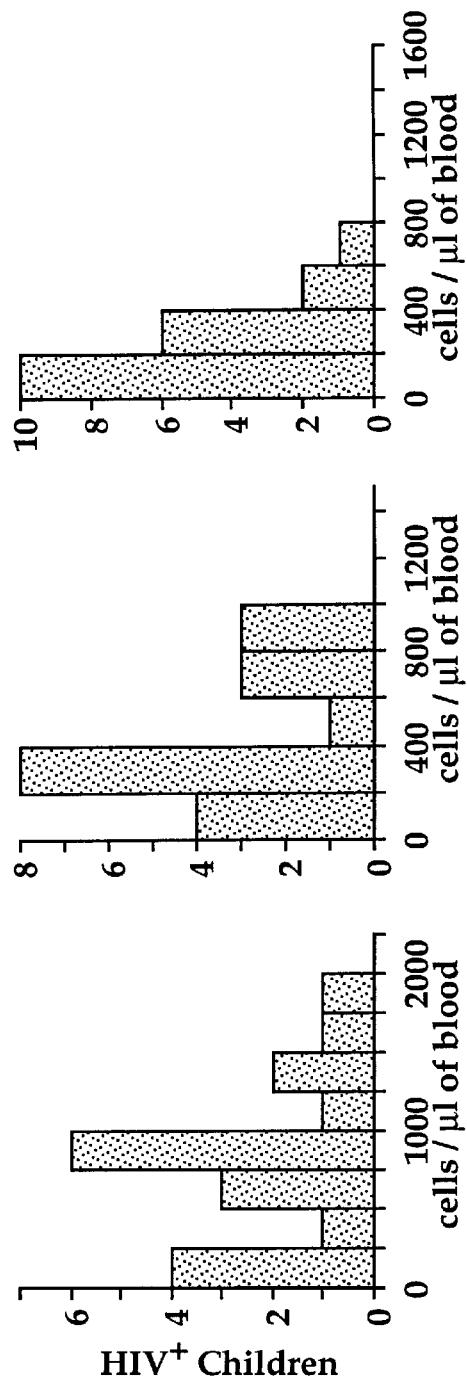

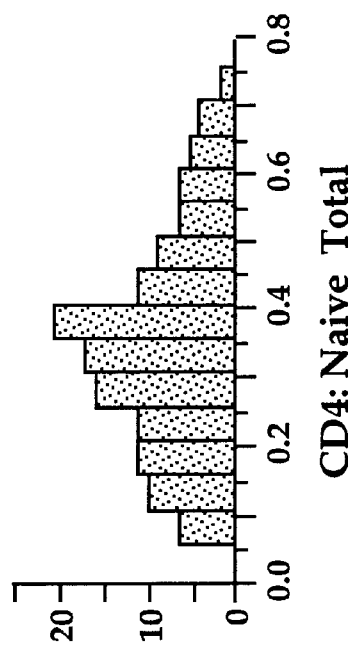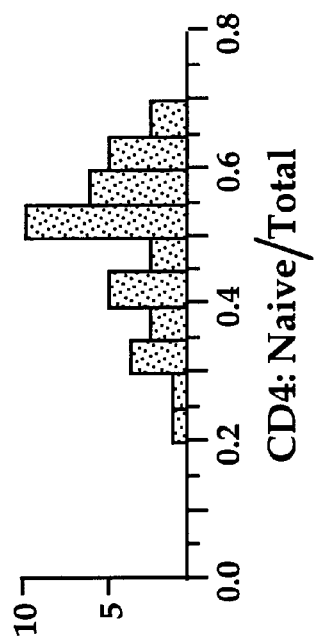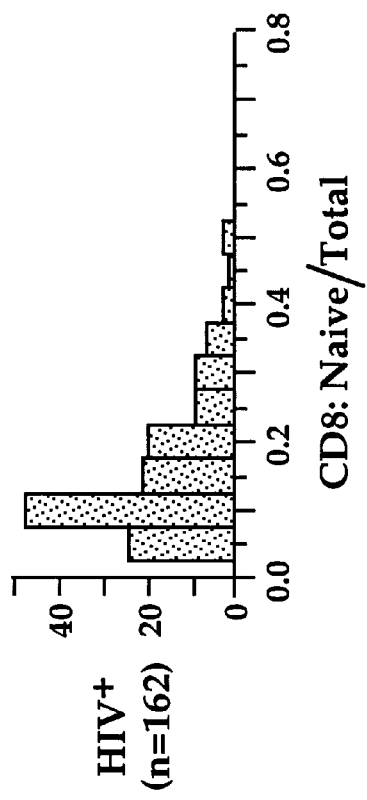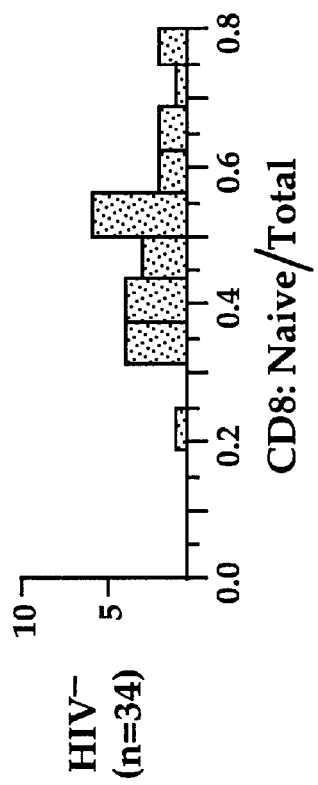

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Beta Actin primer A (xi) SEQUENCE DESCRIPTION: SEQ ID NO:1:

TGACGGGGTC ACCCACACTG TGCCCATCTA                                    30

(2) INFORMATION FOR SEQ ID NO:2:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Beta Actin primer B (xi) SEQUENCE DESCRIPTION: SEQ ID NO:2:

CTAGAAGCAT TGCGGTGGAC GATGGAGGG                                     29

(2) INFORMATION FOR SEQ ID NO:3:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (vi) ORIGINAL SOURCE:
         (C) INDIVIDUAL ISOLATE: Gamma IFN primer A (xi) SEQUENCE DESCRIPTION: SEQ ID NO:3:

ATGAAATATA CAAGTTATAT CTTGGCTTT                                     29

(2) INFORMATION FOR SEQ ID NO:4:

(i) SEQUENCE CHARACTERISTICS:
         (A) LENGTH: 26 base pairs
         (B) TYPE: nucleic acid
         (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Gamma IFN primer B (xi) SEQUENCE DESCRIPTION: SEQ ID NO:4:

GATGCTCTTC GACCTCGAAA CAGCAT                                              26

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: IL-2 primer A (xi) SEQUENCE DESCRIPTION: SEQ ID NO:5:

ATGTACAGGA TGCAACTCCT GTCT                                                24

(2) INFORMATION FOR SEQ ID NO:6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: IL-2 primer B (xi) SEQUENCE DESCRIPTION: SEQ ID NO:6:

GTCAGTGTTG AGATGATGCT TTGA                                                24

(2) INFORMATION FOR SEQ ID NO:7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: IL-4 primer A (xi) SEQUENCE DESCRIPTION: SEQ ID NO:7:

ATGGGTCTCA CCTCCCAACT GCT                                                 23

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: IL-4 primer B (xi) SEQUENCE DESCRIPTION: SEQ ID NO:8:

CGAACACTTT GAATATTTCT CTCTCAT                                      27

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: IL-5 primer A (xi) SEQUENCE DESCRIPTION: SEQ ID NO:9:

GCTAGCTCTT GGAGCTGCCT AC                                           22

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: IL-5 primer B (xi) SEQUENCE DESCRIPTION: SEQ ID NO:10:

TCAACTTTCT ATTATCCACT CGGTGTTCAT TAC                               33

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: IL-10 primer A (xi) SEQUENCE DESCRIPTION: SEQ ID NO:11:

ATGCCCCAAG CTGAGAACCA AGACCC                                                      26

(2) INFORMATION FOR SEQ ID NO:12:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: IL-10 primer B (xi) SEQUENCE DESCRIPTION: SEQ ID NO:12:

TCTCAAGGGG CTGGGTCAGC TATCCC                                                      26

(2) INFORMATION FOR SEQ ID NO:13:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: GM-CSF primer A (xi) SEQUENCE DESCRIPTION: SEQ ID NO:13:

ATGTGGCTGC AGAGCCTGCT GC                                                          22

(2) INFORMATION FOR SEQ ID NO:14:

(i) SEQUENCE CHARACTERISTICS:
              (A) LENGTH: 22 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (vi) ORIGINAL SOURCE:
              (C) INDIVIDUAL ISOLATE: GM-CSF primer B (xi) SEQUENCE DESCRIPTION: SEQ ID NO:14:

CTGGCTCCCA GCAGTCAAAG GG                                                          22

METHODS FOR DETERMINING T-CELL PROFILES OF IMMUNOCOMPROMISED SUBJECTS

This application claims priority to Provisional U.S. patent application Ser. No. 60/004,364, filed Sep. 27, 1995, herein incorporated by reference.

This invention was made with Government support under grants AI-31770, LM-04836, and CA-42509 awarded by the National Institutes of Health. Accordingly, the United States Government has certain rights in this invention.

FIELD OF THE INVENTION

The present invention relates to methods of identifying an abnormal T-cell profile of an immunocompromised subject. More specifically, the invention relates to methods for unambiguously identifying naive T-cells, and the use of these methods in screens for drugs effective to elevate naive T-cell counts in immunocompromised subjects.

REFERENCES

Bell, E. B., and Sparshott, S. M., Nature 348:163–166 (1990).

Bonyhadi, M. L., et al., Nature 363:728–732 (1993).

Borkowsky, W., et al., Clin. Immunol. & Immunopathol. 63:280–284 (1992).

Brosnan, J., et al., U.S. Pat. No. 5,064,616, issued Nov. 12, 1991.

Byrne, J. A., et al., J. Immunol. 141:3249 (1988).

Church, J. A., et al., J. Pediatr. 115:420–423 (1989).

Clement, L. T., J. Clin. Immunol. 12:1–10 (1992).

Cook, R. T., et al., Alcoholism: Clin. & Exper. Res. 18:71–80 (1994).

Coon, J. S., et al. (Eds.), DIAGNOSTIC FLOW CYTOMETRY (Academy of Pathology, Inc.) (1991).

DeJong, R., et al., J. Immunol. 146:2088–2094 (1991).

Ernst, D. N., et al., J. Immunol. 151:575–587 (1993).

Froebel, K. S., et al., AIDS 5:97–99 (1991).

Giorgi, J. V., and Detels, R., Clin. Immunol. & Immunopath. 52:10–18 (1989).

Harlow, E., et al., ANTIBODIES: A LABORATORY MANUAL (Cold Spring Harbor Press, Cold Spring Harbor, N.Y.) (1988).

Keren, D. F., et al. (Eds.), FLOW CYTOMETRY IN CLINICAL DIAGNOSIS (American Society of Clinical Pathologists) (1989).

Mackweicz, C., and Levy, C. A., AIDS Res. Hum. Retroviruses 8:1039–50 (1992).

Mansour, J. D., et al., U.S. Pat. No. 4,622,298, issued Nov. 11, 1986.

Matsuda, S., et al., U.S. Pat. No. 5,039,613, issued Aug. 13, 1991.

McGrath, M. S., "AIDS Knowledge Base" in AIDS KNOWLEDGE BASE: TEXTBOOK ON HIV FROM UCSF AND SF GENERAL HOSPITAL (Cohen, P. T., et al., Eds.), Medical Publishing Group, Waltham, pp. 3.2.2–1–3 (1990).

McGrath, M. S., "T Cell Abnormalities" in AIDS KNOWLEDGE BASE: TEXTBOOK ON HIV FROM UCSF AND SF GENERAL HOSPITAL (Cohen, P. T., et al., Eds.) Medical Publishing Group, Waltham, P. A., pp. 3.2.2–1–3 (1990).

Moore, W. A., and Kautz, R. A., "Data Analysis in Flow Cytometry" in HANDBOOK OF EXPERIMENTAL IMMUNOLOGY (Weir, D. M., et al., Eds.) Blackwell Scientific Publications, Edinburgh, Scotland, pp. 30.1–30.11. (1986).

Mullis, K. B., U.S. Pat. No. 4,683,202, issued Jul. 28, 1987a.

Mullis, K. B., et al., U.S. Pat. No. 4,683,195, issued Jul. 28, 1987b.

Okumura, M., et al., J. Immunol. 150:429–437 (1993a).

Okumura, M., et al., Eur. J. Immunol. 23:1057–1063 (1993b).

Picker, L. J., et al., J. Immunol. 150:1105–1121 (1993).

Powers, L. W., DIAGNOSTIC HEMATOLOGY: CLINICAL AND TECHNICAL PRINCIPLES, The C.V. Mosby Company (1989).

Prince, H. E., et al., J. Acquir. Immune Defic. Syndr. 3:525–530 (1990).

Prince, H. E., and Jensen, E. R., J. AIDS 4:1227–1232 (1991).

Reddy, M. M., and Grieco, M. H., J. Clin. Lab. Anal. 5:96–100 (1991).

Roederer, M., et al., "Disregulation of Leukocyte Glutathione in AIDS" in CLINICAL FLOW CYTOMETRY (Landay, A. L., et al., Eds.) NY Academy of Sciences, New York, pp. 113–125 (1993).

Rothstein, D. M., et al., J. Immunol. 146:1175–1183 (1991).

Sanders, M. E., et al., J. Immunol. 140:1401–1407 (1988a).

Sanders, M. E., et al., Immunol. Today 9:195–199 (1988b).

Semba, R. D., et al., Lancet 341:5–8 (1993).

Smerdon, R. A., et al., Diabetes 42:127–133 (1993).

Sohen, S., et al., Cell. Immunol. 128:314–328 (1990).

Steihm, E. R., and Wara, D. W., "Immunology of HIV" in PEDIATRIC AIDS: THE CHALLENGE OF HIV INFECTION IN INFANTS, CHILDREN, AND ADOLESCENTS (Pizzo, P. A., and Wilfert, C. M., Eds.) Williams and Wilkins, Baltimore, Md., pp. 95–112 (1991).

Swain, S. L., J. Immunother. 14:150–154 (1993).

Teitel, J. M., et al., Am. J. Hematol. 32:262–272 (1989).

BACKGROUND OF THE INVENTION

Clinical evaluation of a patient infected with HIV virus (Acquired Immunodeficiency Syndrome; AIDS) currently relies on physician evaluation of patient status in conjunction with quantitation of T-cell lymphocytes present in the patient's blood. Such cell counts, though reflecting the gross progression of the disease, do not provide specific information concerning either the functional status of the patient's immune system nor the efficacy of particular therapeutic agents in treating the infection, since T-cells comprise a heterogeneous mixture of cell types. There are at least two major subsets of T-cells, termed CD4 and CD8.

Recently, investigators have developed assays which employ fluorescently tagged monoclonal antibodies to specific cell antigens and Fluorescence Activated Cell Sorting (FACS) to determine the relative proportions of the various lymphocyte classes in a patient's blood. Such assays have shown that HIV viral infection differentially affects the various blood cell types. Persons infected with the HIV virus, and particularly those persons characterized as having Acquired Immune Deficiency (AIDS) or Aids Related Complex (ARC) have been shown to have reduced numbers of CD4 cells and, in many cases, elevated proportions of CD8 cells.

In evaluating treatments and/or therapies for AIDS, as well as in determining which existing therapies are most appropriate for a particular AIDS patient, it is important to have an accurate measure of the extent of the disease (i.e., the stage to which the disease has progressed) in the subjects under evaluation, so that results of such studies can be interpreted in a meaningful manner. Such "staging" information has historically been inferred from the total CD4+ T lymphocyte (T cell) counts, which are known to fall progressively as the disease advances.

As is disclosed below, however, the use of total CD4+ T cell counts as a measure of the advancement of AIDS fails to detect aspects and consequences of the disease that are important in the choice of therapies at particular stages, and the evaluation of the effectiveness of experimental therapies.

The present invention provides methods of staging the advancement or progress of AIDS, as well as other diseases and/or conditions affecting the function of the immune system, that are more useful and accurate than total CD4 T cell counts.

SUMMARY OF THE INVENTION

In one embodiment, the present invention includes a method of identifying an abnormal T-cell profile of an immunocompromised subject relative to the T-cell profile of a non-immunocompromised subject. The method includes (i) sorting a sample of peripheral blood mononuclear cells (PBMC) isolated from the immunocompromised subject into sets of T-cell types, (ii) determining the ratio of naive cells relative to the total number of cells (naive:total) in each set, and identifying an abnormal T-cell profile in the immunocompromised subject by comparing the naive:total ratios of sets from the immunocompromised subject with the naive:total ratios of analogous sets from a non-immunocompromised subject.

In a preferred embodiment, the sorting step is carried using a flow cytometer with gates uniquely identifying, for example, CD4 or CD8 T cells and their subsets.

The determining step in the above method is carried out by detecting immunoreactivity of T-cells in the sets with at least two antibodies selectively reactive with naive T-cell surface proteins (such as antibodies CD45RA and CD62L or CD45RA and CD11a). It will be understood that in the course of carrying out the sorting and the determining steps, at least three different antibodies are employed. For example, identification of naive CD4+ T-cells may be accomplished by first sorting the PBMC into sets, one of which contains primarily CD4+ T-cells (as identified with an anti-CD4 antibody), and then determining the naive:total ratio using either CD45RA and CD62L, or CD45RA and CD11a antibodies. of course, as is described more fully below, the sorting and determining steps may be carried out together, using, for example, three-color immunophenotyping FACS.

It will be appreciated that the above method may also be carried out by calculating the absolute number of naive cells, rather than simply the ratio of naive cells relative to the total number of cells (naive:total), in each set. The absolute number of naive cells can be determined from the naive:total ratio and the total T-cell count, as detailed below.

In one general embodiment, the abnormal T-cell profile includes the preferential loss of naive T-cells in the immunocompromised subject. In other general embodiments, the sets of T-cell types include a set consisting essentially of CD4+ and CD8+ T-cells. In related embodiments, the sets can consist of essentially only CD4+ cells or essentially only CD8+ cells.

The immunocompromised subject can be, for example, an HIV-positive, and individual undergoing immunotherapy, a cancer patient, an individual with a viral infection, an individual with an autoimmune disease or the like. The sorting and determining steps of the method may be performed, for example, FACS analysis or panning.

A preferred method for carrying out the sorting and determining steps is using three-color immunophenotyping FACS. In this embodiment, the cells are not physically separated during the sorting step, but merely identified as CD4 or CD8 cells. This identification, as well as the subsequent determining steps, are typically carried out simultaneously. A sample of PBMC is introduced into a three-color immunophenotyping FACS apparatus, and the subsets of CD4 and CD8, as well as naive and memory T-cells are identified.

The methods described above may also be employed to measure the absolute (as opposed to relative) naive T-cell counts (either total T-cell counts, or counts of specific subsets, such as naive CD4+ T-cells and/or CD8+ T-cells). In this general embodiment, absolute counts may be obtained by, for example, multiplying the ratio of naive:total T-cells by the total number of T-cells/$\mu$l (as determined, for example, from blood cell counts).

In another aspect, the present invention includes a method of screening compounds in an animal model or human subject to identify compounds effective to stimulate the production of naive T cells in the model or subject. In one embodiment, drugs are evaluated for their efficacy to stimulate the production of naive T cells in a subject. In the case of human subjects, the drugs employed are preferably those that have been approved for human use.

The method includes the steps of obtaining samples containing peripheral blood mononuclear cells (PBMC) from the animal or subject, both before and after administration of a suitable dose of the drug or compound, isolating populations of T cells from the samples, and determining the number of naive T cells in each population. The determining step includes the detection of immunoreactivity of T-cells in the populations with at least two antibodies selectively reactive with naive T-cell surface proteins. Data from the detection of immunoreactivity are typically analyzed in light of the total blood counts to arrive at the number of naive T-cells in the sample. A drug or compound is identified as effective if the number of naive T-cells in the sample obtained after drug/compound administration is significantly greater than the number of naive T-cells in the sample obtained before drug/compound administration. Significance may be determined by any of a number of statistical methods known to those skilled in the art.

In one general embodiment, the isolating step of the above method includes sorting each sample into sets of T-cell types, and the determining step includes determining the number of naive T cells in each set of each population. Each population may contain, for example, a set of CD4 T-cells and a set of CD8 T-cells, or a set containing both CD4+ and CD8+ T-cells.

These and other objects and features of the invention will become more fully apparent when the following detailed description is read in conjunction with the accompanying drawings.

BRIEF DESCRIPTION OF THE FIGURES

FIGS. 1A, 1B, 1C and 1D show T cell subset phenotypes as determined by scatter gates (FIG. 1A), CD4/CD8 staining (FIG. 1B), and CD45RA and CD62L staining (FIGS. 1C and 1D). These figures were generated from data obtained in the adult study.

FIGS. 2A, 2B, 2C, 2D, 2E, 2F, 2G, 2H, 2I and 2J show 5% probability contour plots of CD8 T cells from a healthy adult (FIGS. 2A and 2B), two HIV-negative control children, ages 28 months (FIGS. 2C and 2D) and 94 months (FIGS. 2E and 2F), and two HIV-infected children, ages 27 months (FIGS. 2G and 2H) and 88 months (FIGS. 2I and 2J). These figures were generated from data obtained in the child study.

FIG. 3A, 3B, 3C, 3D, 3E, 3F, 3G and 3H show examples of CD8 T cell subsets in healthy (FIGS. 3E–H) and HIV-infected (FIGS. 3A–D) adults. Four examples each from the HIV-negative cohort (FIGS. 3E–H) and the HIV+ cohort (FIGS. 3A–D) were selected to show the range of naive T cell representation in these groups. These figures were generated from data obtained in the adult study.

FIGS. 5A, 5B, 5C, 5D and 5E show a functional analysis of CD8 T cell subsets as defined in FIG. 2 using calcium flux measurements. These figures were generated from data obtained in the child study.

FIGS. 7A, 7B, 7C, 7D, 7E and 7F show a distribution of CD8 T cell subsets among HIV-negative control (FIGS. 7A, 7C and 7E) and HIV-infected children (FIGS. 7B, 7D and 7F). FIGS. 7A and 7B show CD8+ cells, FIGS. 7C and 7D show CD8+, CD45RA+ cells and FIGS. 7E and 7F show naive CD8+ cells (CD8+, CD45RA+, CD11a$^{lo}$). These figures were generated from data obtained in the child study.

FIGS. 8A, 8B, 8C and 8D show representations of naive T cells within the CD4 (FIGS. 8C and 8D) and CD8 (FIGS. 8A and 8B) lineages from HIV+ (FIGS. 8A and 8C) and HIV- (FIGS. 8B and 8D) adults. These figures were generated from data obtained in the adult study.

FIG. 10A shows the naive CD8 T cell count plotted against the absolute total CD4 count, FIG. 10B shows the total CD8 count plotted against the absolute total CD4 count, and FIG. 10C shows the absolute number of naive CD4 T cells plotted against the absolute total CD4 count. These figures were generated from data obtained in the child study.

DETAILED DESCRIPTION OF THE INVENTION

I. Definitions

Figure 4A:
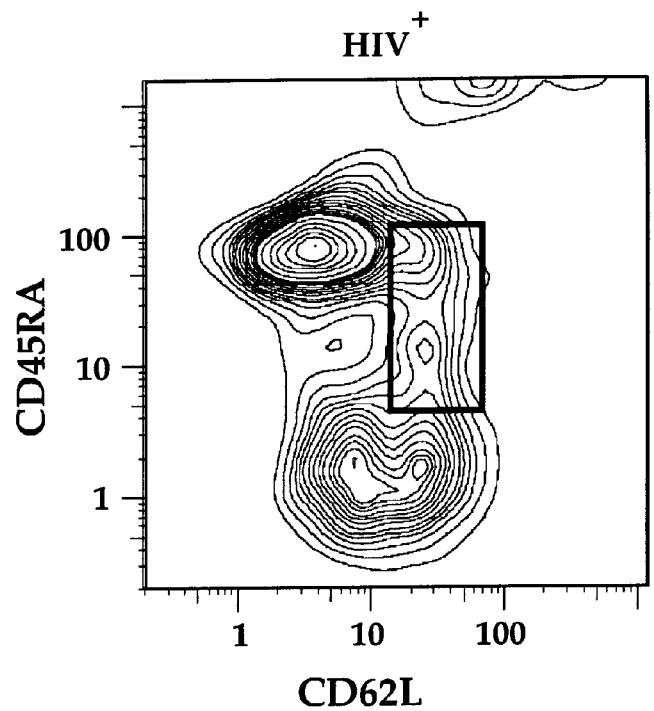
FIGS. 4A and 4B show examples of CD4 T cell subsets in healthy (FIG. 4B) and HIV-infected (FIG. 4A) adults. A comparison of an uninfected individual (FIG. 4B) and an HIV-infected individual (FIG. 4A) is shown, with the box denoting the position of the naive cells. These figures were generated from data obtained in the adult study.

"HIV" is used in the present application to refer to the family of Human Immunodeficiency viruses which includes HIV-1 and HIV-2.

A "T-cell profile" of a subject is a characterization of the distribution of different types of T-cells, e.g., comprising the subject's immune system.

An "abnormal T-cell profile" exists when the relative and/or absolute numbers of certain T-cell types are outside of the values typically found in normal, healthy individuals. For example, experiments detailed herein demonstrate that the ratio of naive to total T-cells in the CD4 and CD8 sets of T-cells isolated from AIDS patients (immunocompromised subjects) is lower than it is in individuals not infected with HIV (non-immunocompromised subjects). Such an abnormal ratio is an indicator of an abnormal T-cell profile.

An "immunocompromised subject" is an individual whose immune system is compromised or not functioning in a normal manner. For example, AIDS patients and patients undergoing immunotherapy are immunocompromised subjects. Further, various other conditions, such as certain cancers, viral infections and autoimmune diseases may render the affected individuals immunocompromised. Individuals who have undergone stem cell replacement therapy, bone marrow transplant, chemotherapy, radiotherapy and the like are also typically immunocompromised subjects.

A "set of T-cell types" refers to one of the major functionally-distinct classes of T-cells that can be distinguished based on cell surface marker expression. Two exemplary sets of T-cell types are the set expressing CD4 (CD4+ T-cells) and the set expressing CD8 (CD8+ T-cells). Of course, a set can consist of several such classes of T-cells. For example, a single set can include both CD4+ and CD8+ T-cells.

A "subset" of T-cell types refers to a functionally-distinct class of T-cells from a set of T-cell types. For example, naive CD4+ T-cells are a subset of the set consisting of CD4+ T-cells. "Analogous sets" are sets of T-cell types defined based on the same characteristics as the sets to which they are analogous, but isolated from a different individual. For example, the set of CD4+ cells isolated from an immunocompromised subject is analogous to the set of CD4+ cells isolated from a non-immunocompromised subject.

"Antibodies selectively reactive with naive T-cell surface proteins" are antibodies directed against antigens that are recognized, either based on experimental evidence or on general knowledge in the art, as being preferentially-expressed on the surface of naive T-cells (as opposed to memory T-cells). Such antigens are not necessarily expressed exclusively on naive cells.

"Sorting" in the context of cells (e.g., "sorting a sample of peripheral blood mononuclear cells") is used herein to refer to both physical sorting of the cells, as can be accomplished using, e.g., a fluorescence activated cell sorter, as well as to classifying (in the absence of physical separation) the cells based on expression of cell surface markers. The classifying may be done, for example, by simultaneously analyzing the expression of several (e.g., 3) markers, and determining the number and/or relative number of cells expressing different combinations of the markers (e.g., with the aid of a computer running a FACS analysis program).

"FACS" was originally coined as an acronym for Fluorescence Activated Cell Sorting, where the "Sorting" referred to physical separation of the cells into different containers. More recently, the use of term has broadened to include references to procedures and/or machines/instruments that relate to fluorescence analyses on a population of cells that result in a quantification of the number or relative number of cells having selected levels of reporter fluorescence. The term "FACS" as used herein refers to the more recent, broader definition of the term.

The term "significantly", when used in a context such as "significantly different", "significantly inhibits" or "significantly stimulates", "significantly greater", or "significantly smaller", refers to a difference in a quantifiable parameter between the two groups being compared that is statistically-significant using standard statistical tests. For example, the number of naive T-cells may be quantified using standard methods (e.g., as described herein), and the number of naive T-cells present under different conditions can be compared for statistically-significant differences (e.g., using standard error of the mean (SEM)).

II. T-Cell Markers

CD4+ and CD8+ T lymphocytes, or T-Cells, can be subdivided into several phenotypically and functionally-distinct subsets (Sanders, et al., 1988; Sohen, et al., 1990;

DeJong, et al., 1991; Picker, et al., 1993; Okumura, et al., 1993a). Functional studies have assigned specific roles to some of these subsets. In particular, the terms "memory" and "naive" distinguish subsets which either contain or do not contain (respectively) long-lived cells capable of mounting an immediate response to a specific antigen. In vitro studies have also demonstrated that these subsets have distinct functional capacities: in general, the memory subsets do not proliferate as well as naive subsets in response to generic mitogenic stimuli; however, the memory subsets produce a wider variety and greater amounts of many cytokines (Sanders, et al., 1988b; Swain, 1993; Ernst, et al., 1993).

In particular, CD8 T cells, which provide cell mediated immunity through both cytotoxic and suppressor mechanisms (Mackweicz and Levy, 1992), can be subdivided by multiparameter flow cytometry into subsets according to the differential expression of surface proteins. The naive subset expresses the CD45RA surface marker (CD45RA$^{hi}$), and makes a relatively poor cytokine response after T cell receptor stimulation. In contrast, the memory subset expresses CD45RO (another isoform of CD45$^3$) instead of CD45RA (DeJong, et al., 1991; Clement, 1992).

III. T-Cells and AIDS

Studies characterizing changes in T cell representation in Acquired Immune Deficiency Syndrome (AIDS) have generally focused on the decrease in total CD4$^+$ T-cell count (CD4 count) that occurs as the disease progresses. Indeed, for over a decade, the specific loss of these cells has been the most commonly-used surrogate marker for disease progression.

Unlike CD4 T cell counts, absolute CD8$^+$ T-cell counts (CD8 counts) have been shown to rise early after HIV infection and maintain a relatively steady level until very late in the disease (Giorgi and Detels, 1989), when CD4 counts drop below 100/$\mu$l (McGrath, 1990; Steihm and Wara, 1991). Naive CD8 T cell frequencies, estimated on the basis of CD45RA expression alone, were found to decrease little (Prince, et al., 1990; Giorgi and Detels, 1989), or not at all (Teitel, et al., 1989).

Most previous attempts to quantitate the relative levels of "naive" and "memory" subsets showed little or no preferential loss of either subset during the progression of AIDS (Giorgi and Detels, 1989; Reddy and Grieco, 1991; Prince, et al., 1990; Teitel, et al., 1989), although memory CD8 T cell frequencies, estimated on the basis of CD45RO expression (Froebel, et al., 1991; Borkowsky, et al., 1992), were found to increase in infected children. The methodology used in these studies, however, did not definitively resolve the naive and memory subsets, since the shift from CD45RA$^{hi}$ to CD45RO (CD45RA$^-$) is reversible. Accordingly, not all CD8 T cells that expressed the CD45RA$^{hi}$ (CD45RO$^-$) phenotype were naive (Bell and Sparshott, 1990; Rothstein, et al., 1991).

Experiments performed in support of the present invention and described below definitively resolve the memory and naive subsets by employing three-color multiparameter flow cytometry to simultaneously measure CD8, CD45RA, and either CD11a (LFA-1α; Sanders, et al., 1988b) or CD62L (L-selectin; LECAM; Picker, et al., 1993).

IV. Summary of Studies and Experiments

Three-color immunophenotyping was used to address the impact of HIV infection on the representation of defined T cell subsets in adults and children. By specifically distinguishing the naive T cells from those in various memory subsets, a preferential loss of the naive T cells that correlates with progression of HIV disease (as measured by the decline of total CD4 T cells) was observed. Significantly, the loss of the naive cells began relatively early after infection, when the individuals were otherwise asymptomatic and still had substantial numbers of CD4 T cells. In addition, data are presented which demonstrate that the number of naive CD8 T cells correlates with the number of total CD4 T cells in both children and adults. Specifically, data detailed below demonstrated a clear loss of the naive subset of CD8 T cells and an increase in CD8 memory T cells in HIV-infected individuals.

These findings revealed a previously unsuspected complexity in the dynamics of T cell representation in HIV-infected individuals. Despite the progressive decrease of naive CD8 T cells, the overall CD8 T cell number persisted at elevated levels until very late in the disease. The increased numbers of CD8 T cells therefore reflect a selective increase in memory CD8 T cells. Since naive T cells are memory precursors, their loss may contribute substantially to the eventual loss of the total CD8 population.

These changes in the CD8 cell subsets may contribute to the increased susceptibility to infection and the loss of cell mediated immunity that is observed in HIV-infected individuals. Together, the adult and child studies demonstrate that loss of the functionally important naive T cells from both CD4 and CD8 lineages is characteristic of HIV infection, and suggest that the loss of these cells may play a major role in the immunopathogenesis of HIV disease. Because naive T cells are so important for the generation of new immune responses, the naive counts may be used to stratify clinical trials of therapeutic vaccinations and immunomodulatory therapies in HIV disease, and to screen for immunomodylatory drugs.

A. Child Study—Summary

In HIV-negative children, the naive subset was present at high frequencies, whereas memory cells were virtually absent. Previous studies have shown that the overall number of CD8 T cells does not decrease in HIV-infected children. In studies described below, it is demonstrated that within the CD8 T cell population, the naive subset decreases markedly (HIV$^+$ vs. HIV$^-$, 190 vs. 370 cells/$\mu$l; p≦0.003), and that there is a reciprocal increase in memory cells, such that the total CD8 T cell counts remained unchanged (800 vs. 860 cells/$\mu$l; p≦0.76). In addition, it is demonstrated that for HIV-infected children, the naive CD8 T cell and total CD4 T cell counts correlate (chi-square, p≦0.001). This correlated loss suggests that the loss of naive CD8 T cells in HIV infection may contribute to the defects in cell mediated immunity which become progressively worse as the HIV disease progresses and CD4 counts decrease.

B. Considerations for Interpretation of Data in Child Study

Studies performed in support of the present invention and described herein compare HIV-infected children with control patients who were seen in a large pediatric endocrinology clinic. All of the control children were growing parallel to the normal growth curve and none was receiving steroid therapy; most were being followed for isolated problems such as congenital hypothyroidism or possible or actual growth hormone deficiency. Children with multiple endocrinopathies, such as hypopituitarism, were rejected from this study because growth hormone affects CD4 T cell counts in these children (Church, et al., 1989). Since findings with control children receiving therapy did not differ from findings with controls who were in no need of therapy (e.g., normal variant short stature), it is unlikely that the corrected hormonal deficiencies of some of the children confound their immunologic status.

The conclusions drawn from the results of the child study are also not confounded by possible differences between chronological and physiologic ages in control and HIV-infected groups of children, nor the broad age range of the children studied. Okumura and colleagues, using CD8 T cell subset definition criteria similar to those used herein (CD11a, CD45RA), demonstrated changes in the frequencies of CD8 T cell subsets that begin to occur during adolescence in healthy individuals (Okumura, et al., 1993b). The children employed in the present study (both the HIV-negative control and HIV-infected groups) were all under 13 years of age. In these preadolescent children, no evidence was found that frequency of subsets correlates with age. Thus, it appears that age was not a factor in the present studies involving children.

C. Adult Study—Summary

In adults, CD8 naive T cells were depleted during the asymptomatic stage of HIV infection. Although overall CD8 T cell numbers were increased during this stage, the naive CD8 T cells were progressively lost, and fell in parallel with overall CD4 T cell counts. In addition, it is shown that naive CD4 T cells were preferentially lost as total CD4 cell counts fall. These findings represent the first demonstration that HIV disease involves the loss of both CD4 T cells and CD8 T cells.

The adults studies also show that the well-known increase in total CD8 counts in most HIV-infected individuals is primarily due to an expansion of memory cells. Thus, memory CD8 T cells account for over 80% of the T cells in PBMC from individuals with less than 200 CD4/$\mu$l, whereas they account for roughly 15% of T-cells in uninfected individuals. Since the naive and memory subsets have very different functional activities, this altered naive/memory T cell representation has significant consequences for the interpretation of data from in vitro functional studies.

D. Naive T Cells

Functionally, naive T cells are defined as cells which have recently emigrated from the thymus and have a predominantly proliferative response when exposed to cognate antigens for the first time (DeJong, et al., 1991; Byrne, et al., 1988). This encounter with antigen also triggers the naive T cell to differentiate and express the surface phenotype of memory cells (Picker, et al., 1993). Thereafter, when a memory T cell encounters its cognate antigen, the response is predominantly one of cytokine secretion rather than proliferation (DeJong, et al., 1991).

Accepted definitions of naive and memory cells (Sanders, et al., 1988a; Picker, et al., 1993) were confirmed by experiments performed in support of the present invention: the naive cells showed a greater capacity to flux calcium and to proliferate in response to mitogenic stimuli, but had a more limited cytokine response than memory/effector cells. However, the results, which demonstrate that naive CD8 T cells decrease substantially in HIV-infected individuals, conflict with earlier observations indicating that naive CD8 T cell counts either decrease slightly or remain unchanged (Giorgi and Detels, 1989; Teitel, et al., 1989; Borkowsky, et al., 1992; Reddy and Grieco, 1991; Prince and Jensen, 1991; Froebel, et al., 1991).

According to the teachings herein, these differences are explained by the difference in methodology used to identify the naive cells: in contrast to previously-used methods, the use of the three-color immunofluorescence profile employed in the present experiments resolves the naive cells completely from the memory subsets.

E. Possible Mechanisms for Naive T Cell Loss

Although not wishing to be bound by any particular mechanism for the observations described herein, there are several possibilities for the loss of circulating naive CD8 T cells in HIV-infected individuals. For example, the loss could be due to HIV infection of early "double-positive" progenitors in the thymus. Bonyhadi and colleagues have shown that CD4+ CD8+ T cell progenitors can be infected and thereby die before emigrating from the thymus and entering the peripheral circulation as naive T cells (Bonyhadi, et al., 1993). Accordingly, the loss of naive CD8 T cells may be due to the depletion of these double positive precursors. This mechanism could be important in children because the thymopoiesis is extremely active prior to adolescence.

Figure 10A:
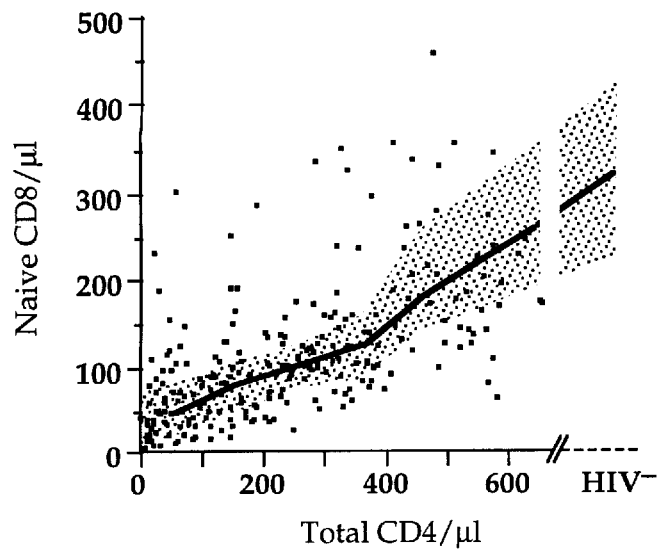
FIGS. 10A, 10B and 10C show plots of the correlation of naive T cell representation with absolute CD4 count.
Figure 10B:
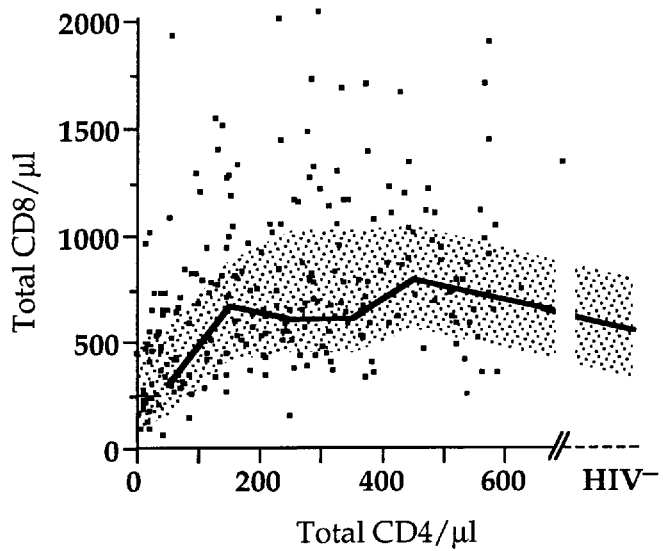
Figure 10C:
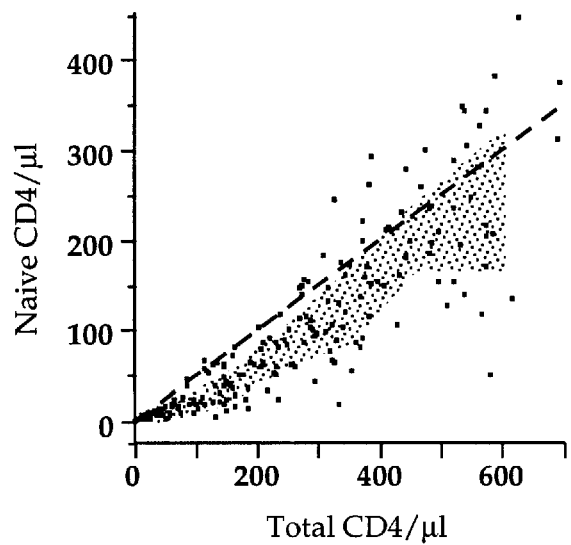

Alternatively, loss of thymopoietic capability could be due to a general destruction of the thymus or a progressive loss of the bone marrow's capacity to produce thymocyte progenitors. Hypotheses based on general failure of thymopoiesis are attractive since they could also explain the preferential loss of naive CD4 T cells (FIGS. 10A–C).

Alternatively, the decrease in naive CD8 T cells may not be primarily due to HIV infection, but may be secondary to complications of HIV which are perhaps common to all chronic infections or inflammatory states. In fact, CD8, CD45RA$^{hi}$ T cells are decreased in adults with long-standing insulin dependent diabetes (Smerdon, et al., 1993), and vitamin A deficient children have increased CD45RO$^{hi}$, CD8 T cells (Semba, et al., 1993). Similarly, chronic alcohol consumption by adults frequently results in a loss of T cell function and a concomitant decrease in the representation of naive T cell subsets (Cook, et al., 1994). But whether the decline in naive CD8 T cells is unique to HIV, or occurs more generally in severe disease, is irrelevant to the immunopathogenic consequences of the loss of these cells. Since naive T cells are crucial to immune responsiveness, their loss may have as severe an impact in HIV disease as the overall loss of CD4 T cells.

In particular, HIV-infected individuals with low CD4 T cell counts are more susceptible to infection with opportunistic organisms such as *Pneumocystis carinii* (PCP) and *Mycobacterium avium intracellulare* (MAI). This immune deficiency has been ascribed to the decrease of CD4 T cells. However, data presented herein show that the naive CD8 T cell counts correlate with the total CD4 count. Thus the immunodeficiency in HIV disease could be mediated either by low CD4 counts, low naive CD8 T cell counts or a combination of both, perhaps in conjunction with other factors.

V. Alternative Analysis Methods

The present invention may be performed using methods other than the multiparameter cytometry techniques described in the Examples below, e.g., standard flow cytometry methods. Flow cytometry measure physical and/or chemical characteristics of individual cells carried by a fluid stream past one or more detecting device. Such detecting devices include, but are not limited to, optical and electronic sensors (Coon, et al., 1994). Flow cytometry is in use in clinical settings for cell classification: in particular, the classification of immune system cells. Flow cytometers are available from a variety of suppliers including Coulter Electronics (Hileah, Fla.) and Becton Dickinson (San Jose, Calif.). Flow cytometers which allow multiparametric analysis range from bench top diagnostic models to fluorescence activated cell sorters.

Flow cytometers allow multiple measurements to be made of particles, e.g., cells, under study. With multiparameter cytometry quantitative interrelationships of certain measurable variables, for example, forward and orthogonal light scattering (Keren, et al., 1989; Coon, et al., 1994), or use of specific characteristics, for example, fluorescent detection of cell surface antigens, are used to identify cells as members of particular cell subpopulations. As described herein, it is possible, for example, to define a light scattering gate to include only lymphocytes, in a peripheral blood sample, by placing upper and lower limits on the forward and 90° scatter distributions (Keren, et al., 1989; Matsuda, et al., 1991).

Typically, in the context of the present invention, fluorescent reagents are used as probes to identify specific T-cell surface markers (Keren, et al., 1989; Brosnan, et al., 1991). These reagents allow use of the flow cytometer to provide quantitative analysis of various cellular characteristics, such as cell surface antigens (e.g., $CD4^+$ or $CD8^+$ cell surface antigen). As described herein, multiparameter measurements (e.g., three color measurements) of T-cell surface antigens provide valuable information about the interrelationships of these cellular characteristics.

Most parameters measurable by fluorescence flow cytometry can also be measured by other techniques of analytical cytology, including microfluorimetry (Mansour, et al., 1986) and standard microscope based cytometric analysis. Alternatively, T- and/or B-cells can be physically sorted by panning and expression of other antigens determined by, e.g., standard immunohistochemical techniques.

VI. Utility

A. Implications for Treatment of AIDS and Other Immunosuppressive Conditions

Total CD4 counts, while epidemiologically relevant to AIDS, have long been considered to be a poor surrogate marker. According to data presented herein, this may be because the total CD4 count is be less relevant to the immunopathology of AIDS than naive T-cell counts, which take into account both the CD4 and CD8 arms of the immune system. This is supported by the observation that the total CD4 count is only loosely correlated with the naive T cell counts (in the same sense that it is only loosely correlated with the immunopathology of AIDS). As the naive T-cell subsets disappear, there is a progressive inability to mount responses to novel antigens, which results in higher susceptibility to opportunistic infections. The eventual loss of the naive T-cells predicates the onset of the final stage of AIDS.

The impairment of immune function due to the loss of naive T cells from HIV-infected individuals also has important consequences for therapeutic strategies for AIDS. Since responses to novel antigens arise (by definition) from the naive compartment, the magnitude and effectiveness of such responses are necessarily dependent on the availability of naive T cells. Therefore, an HIV-infected individual with no naive T cells is likely to fail to respond to any primary immunization involving T cells, be it therapeutic vaccination or otherwise. As a practical matter, this means that therapeutic vaccination trials can be severely compromised by failure to control for the variability in the number of naive T cells in study subjects.

Measurement of the absolute numbers of naive T-cells may be a useful indicator in prognosis, diagnosis, or clinical staging. The presence or absence of these cells probably will predict whether or not a person can respond to immunomodulatory therapies, such as therapeutic vaccination. (An infected adult with no naive T cells will not respond to vaccinations, since the naive cells are those which are recruited for this response).

This measurement has important implications in the analysis of clinical trials. According to the results presented herein, patient groups in future trials will preferably be stratified by the naive T-cell counts, much as they are presently stratified by total CD4 counts. Further, naive T-cell counts may be employed for the determination of therapies: using the information disclosed herein, different therapies can be designed for people who retain a substantial number of naive cells than for those who have lost most of them.

Similar considerations apply to therapies involving immunomodulators and ex vivo expansion of cytotoxic T lymphocytes (CTL) for therapeutic re-infusion. Since the representation of CTL precursors and CTL effector cells changes dramatically during the progression of AIDS, the effectiveness of these therapies (or the ability to expand cells capable of carrying out immunity) may vary significantly between patients, due to the variable representation of CD8 subsets. Thus, the findings detailed herein suggest that therapeutic trials for vaccines and immunomodulating methodologies should be stratified with respect to naive T cell count in addition to total CD4 count. Efficacy trials for therapeutic drugs should similarly benefit from this type of stratification, which would eliminate the confounding variable of nonresponsiveness due to the lack of naive T cells.

The loss of naive T cells coupled with the relative over-representation of memory CD8 T cells introduces the necessity for re-examination of all conclusions drawn from functional studies of peripheral blood mononuclear cells (PBMC) from HIV-infected individuals. Memory subsets are the primary producers of certain cytokines such as IL-4, IL-10, and g-IFN; naive subsets tend to produce mainly IL-2. Therefore, simply changing the representation of these functionally distinct subsets would change the cytokine profile of a culture.

For example, cultures of PBMC from a typical HIV-infected individual with less than 100 $CD4/\mu l$ typically have very few naive T cells, and an over-representation of memory CD8 cells. Thus, even if the functions of naive and memory cells are equivalent in HIV-infected and uninfected individuals, PBMC cultures from the HIV-infected individuals would produce less IL-2 and more IL-4 than in comparable cultures from the uninfected individuals. Similarly, since naive T cells proliferate better in response to mitogen than do memory cells, the PBMC cultures from HIV-infected individuals with few naive T cells would proliferate less in response to, e.g., phytohemagglutinin. These results suggest that previous demonstrations of such functional differences between PBMC from individuals at different stages of disease (or between PBMC from infected versus uninfected donors) could merely reflect differences in the underlying representation of naive and memory cells.

The loss of T cells and the impairment of T cell functionality are hallmarks of HIV disease. However, such deficiencies are not restricted to this disease. For example, chronic alcohol consumption frequently results in a loss of T cell function and a decreased representation of naive T cell subsets (Cook, et al., 1994). Thus, the mechanisms underlying the naive T cell loss in HIV disease may reflect general immunoregulatory processes that HIV infection sets in motion.

B. Screening Drugs or Compounds

In another aspect, the present invention includes a method of screening drugs/compounds in an animal model or human subject to identify drugs/compounds effective to stimulate the production of naive T cells in the model or subject. In one embodiment, drugs are evaluated for their efficacy to stimulate the production of naive T cells in a subject.

The method includes the steps of obtaining blood samples containing peripheral blood mononuclear cells (PBMC) from the animal or subject, both before and after administration of a suitable dose of the drug or compound, isolating populations of T cells from the samples, and determining the number of naive T cells in each population (e.g., as described herein). The determining step includes the detection of immunoreactivity of T-cells in the populations with at least two antibodies selectively reactive with naive T-cell surface proteins. Data from the detection of immunoreactivity are typically analyzed in light of the total blood counts to arrive at the number of naive T-cells in the sample. A drug or compound is identified as effective if the number of naive T-cells in the sample obtained after drug/compound administration is significantly greater than the number of naive T-cells in the sample obtained before drug/compound administration.

In one general embodiment, the isolating step of the above method includes sorting each sample into sets of T-cell types, and the determining step includes determining the number of naive T cells in each set of each population. Each population may contain, for example, a set of CD4 T-cells and a set of CD8 T-cells, or a set containing both CD4+ and CD8+ T-cells.

The method is preferably performed as a standard clinical study, with control and experimental groups of individuals. The control individuals preferably receive placebo in the same manner as the experimental group receives the drug/compound being tested. It will be understood that the statistical comparisons used to evaluate the effectiveness of the test drug/compound in stimulating or enhancing production of naive T-cells may be done between the experimental and control groups as a whole, rather than, or in addition to, analysis of data from a particular individual before and after drug treatment. Methods for performing such statistical analyses are known in the art.

The dose of the drug administered is determined based on the pharmacokinetics and bioavailability of the particular drug being tested using standard principles and techniques known in the art. Methods for preparing such dosages are known or will be apparent to those skilled in the art; for example, see *Remington's Pharmaceutical Sciences* (1980).

Any suitable mode of drug administration may be employed. For example, oral administration, nasal insufflation, suppository, parenteral injection, such as intravenous or subcutaneous injection, as well as implantable devices, transdermal delivery devices (e.g., "patch" application) and the like. For oral administration, the drug is typically formulated with an excipient or carrier. Examples of suitable excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers. Injectable compositions for parenteral administration will typically contain the selected test drug or an acceptable salt thereof in a suitable IV solution, such as sterile physiological salt solution. The composition may also formulated as a suspension in a lipid or phospholipid, in a liposomal suspension, or in an aqueous emulsion.

It will be understood that the number of naive T cells in the sample obtained before drug administration may be determined, e.g., using the methods described herein, before determination of the number of naive T cells in the sample obtained after drug/compound administration. In the typical course of events, the pre-treatment sample is obtained and sent to the lab for analysis, the drug/compound treatment program is initiated, and following completion of the drug treatment (which may last days to weeks), the post-treatment sample is obtained and analyzed for the number of naive T cells.

The duration of drug treatment is determined by the scientist or physician performing the study based on known characteristics of the drug/compound being tested. For example, a study may employ a treatment whereby the drug is administered daily for approximately one week.

A variety of drugs or compounds may be evaluated using the methods of the invention. Drugs which have been approved for use in humans are particularly suitable for use in human studies. Other types of compounds which may be evaluated, particularly in animal models, include peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies and specialty suppliers of libraries (e.g., combinatorial libraries) of compounds.

The following examples illustrate but in no way are intended to limit the present invention.

MATERIALS AND METHODS

Ficoll-Hypaque was obtained from Pharmacia (Uppsala, Sweden). Biotin and flavin-deficient RPMI-1640 (hereafter, RPMI) was obtained from Irvine Scientific (Santa Anna, Calif.). Unless otherwise indicated, other chemicals were obtained from Sigma Chemical Co. (St. Louis, Mo.).

A. Subjects—Children

Twelve HIV-infected children were recruited from the outpatient clinics at Children's Hospital Oakland (CHO), and seven from Lucille Packard Children's Hospital (LPCH) at the Stanford University Medical Center. All HIV-infected children were receiving antiretroviral therapy (either Azidothymidine (AZT), dideoxyinosine (DDI), or dideoxycytosine (DDC), or some combination thereof). All children followed at CHO, and two children at LPCH were receiving monthly intravenous immunoglobulin therapy.

The children who served as HIV-negative controls were recruited from the Pediatric Endocrinology Clinic at LPCH. All children accepted into the study had no risk factors for HIV infection. The HIV-negative controls either were considered healthy and in no need of therapy, or were isolated growth hormone or isolated thyroid hormone deficient and were being treated with replacement therapy. Children were rejected from the study if they were receiving steroid therapy, had a history of cancer, had a CD4:CD8 ratio of less than one, or were not growing parallel to the normal growth curve.

The study groups consisted of nineteen HIV-infected and seventeen HIV-negative control children (see Table 1, below). Of the HIV-negative control children, five children (29%) with congenital hypothyroidism (CHT) were being treated with L-thyroxine (Synthroid, Boots Pharmaceutical, Lincolnshire, Ill.), and the five (29%) who were growth hormone deficient (GHD) were receiving recombinant human growth hormone (Protropin, Genentech, South San Francisco, Calif.). Those diagnosed as normal variant short stature (29%, NVSS) and "other" (12%) were not receiving therapy of any kind.

Of the 19 HIV-infected children, five (26%) acquired the virus through contaminated blood products; three of these children have AIDS. The remaining 14 (74%) HIV-infected children acquired the virus vertically; five of them have AIDS.

TABLE 1

CHILD STUDY SUBJECTS

|  | HIV NEGATIVE CONTROL | HIV-INFECTED |
|---|---|---|
| Age |  |  |
| 10–24 months | 1 | 1 |
| 3–4 years | 4 | 7 |
| 5–8 years | 3 | 4 |
| 9–13 years | 6 | 7 |
| 14–16 years | 3 | 0 |
| Median year | 9.8 | 5.7 |
| Sex |  |  |
| Male | 12 | 8 |
| Female | 5 | 11 |
| Mode of Transmission |  |  |
| Vertical |  | 14 (4)[1] |
| Horizontal |  | 4 (2) |
| Diagnosis |  |  |
| CHT[2] | 5 |  |
| GHD | 5 |  |
| NVSS | 5 |  |
| Other | 2 |  |
| T Cell Counts (Median) |  |  |
| CD4[3] | 1320 | 626 |
| CD8 | 875 | 764 |

[1] In parentheses, number of children with AIDS.
[2] CHT, congenital hypothyroidism; GHD, growth hormone deficiency; NVSS, normal variant short status; Other, healthy children in whom disease has been ruled out.
[3] $P < 0.0005$ by Mann-Whitney U non-parametric testing.

B. Subjects—Adults

266 HIV-infected adults were recruited from the San Francisco area. This study was part of a clinical trial in which an entry criterion was less than 500 CD4 T cells per $\mu$l, the cohort is weighted towards infected individuals with fewer CD4 T cells than the general infected population. Also excluded from participation were patients who had concurrent opportunistic infections, or were taking very large amounts of antioxidants, vitamins, or minerals. The infection status of each individual was confirmed by anti-p24 ELISA. In addition, 44 HIV-uninfected adults in good health, were recruited as control subjects. All clinical trial subjects signed an informed consent form.

C. Blood Samples

Blood was drawn by venipuncture for FACS analysis from each HIV-infected patient. In 242 of the 266 adult patients, blood was drawn for a complete blood count (CBC) and an absolute CD4 and CD8 count. From adult control subjects, only blood for FACS analysis was drawn. Samples drawn for FACS analysis were placed in a heparinized tube. All samples were analyzed within 8 hours of the draw.

Three ml of blood were obtained with informed consent from each child and placed in a heparinized tube for analyses as described below. The child study was approved by the Institutional Review Boards of Children's Hospital Oakland and Stanford University Medical Center.

General blood cell counting techniques and DNA quantitation are described by Powers (1989); Keren, et al., (1989); and Coon, et al., (1994).

D. Calcium Flux Measurements

Cells were pre-loaded for 45 min with 10 $\mu$g/ml Indo-1 (Molecular Probes, Eugene, Oreg.) at 37° C. Prior to multiparameter FACS analysis, stained cells were warmed for 5 min to 37° C. A baseline value for the ratio of Indo-1 fluorescences was collected for 30 sec; then 10 $\mu$g of anti-CD3 antibody G19-4 (Dr. J. Ledbetter, Bristol-Meyers Squibb Pharmaceutical Research Institute, Seattle Wash.) was added to the cells. FACS analysis was continued for up to 15 min. The ratio of Indo-1 fluorescences collected in the violet (395–415 nm) and in the green (515–560 nm) was quantified.

E. Proliferation Measurements

Cells from the CD8 subsets were physically sorted (>99% purity, as assessed by reanalysis of physically-sorted cells), and 5,000 cells were deposited in V-bottom wells containing a total of 100 $\mu$l of RPMI medium supplemented with 10% fetal calf serum (Gibco/BRL), and stimulated with combinations of 20 nM phorbol myristate acetate, 50 ng/ml anti-CD3 (Leu4), 1 $\mu$g/ml staphylococcus enterotoxin A, and 20,000 irradiated P815/B7 cells (Lewis Lanier, DNAX Institute, Palo Alto, Calif.). Cells were maintained in culture for 3 days, after which 1 $\mu$Ci of $^3$H-thymidine was added. After an additional 18 hours, cells were harvested and cell-bound radioactivity was quantitated.

F. Cytokine Analyses

Cells from the CD8 subsets were physically sorted (>99% purity, as assessed by reanalysis of physically-sorted cells), and 50,000 of the sorted cells were deposited into pre-warmed (37° C.) medium containing stimulants. After 6 hours, RNA was isolated using RNAzol B (TelTest, Inc., Friendswood, Tex.). Total cDNA was synthesized using 1 $\mu$g of random hexamers in a 20 $\mu$l reaction volume. One-tenth of each cDNA was then amplified by PCR using primers specific for each cytokine; products were separated on a 2% agarose gel and visualized by ethidium bromide staining. Primers for β-actin were also used to verify equivalent recovery of mRNA from the cells. The following primer pairs were used:

β-actin, TGACGGGGTCACCCACACTGTGCCCATCTA (SEQ ID NO:1), CTAGAAGCATTGCGGTGGAC-GATGGAGGG (SEQ ID NO:2);

γ-IFN, ATGAAATATACAAGTTATATCTTGGCTTT (SEQ ID NO:3), GATGCTCTTCGACCTCGAAACAGCAT (SEQ ID NO:4);

IL-2, ATGTACAGGATGCAACTCCTGTCT (SEQ ID NO:5), GTCAGTGTTGAGATGATGCTTTGA (SEQ ID NO:6);

IL-4, ATGGGTCTCACCTCCCAACTGCT (SEQ ID NO:7), CGAACACTTTGAATATTTCTCTCTCAT (SEQ ID NO:8);

IL-5, GCTAGCTCTTGGAGCTGCCTAC (SEQ ID NO:9), TCAACTTTCTATTATCCACTCGGTGTTCATTAC (SEQ ID NO:10);

IL-10, ATGCCCCAAGCTGAGAACCAAGACCC (SEQ ID NO:11), TCTCAAGGGGCTGGGTCAGCTATCCC (SEQ ID NO:12);

GM-CSF, ATGTGGCTGCAGAGCCTGCTGC (SEQ ID NO:13), CTGGCTCCCAGCAGTCAAAGGG (SEQ ID NO:14).

G. Antibodies

General protocols for standard antibody methods are described by Harlow, et al. (1988). Reagents for use in antibody methods are available from the sources listed below and from Pierce (Rockford, Ill.).

The following conjugate monoclonal antibodies were obtained from Becton Dickinson Immunocytometry Systems (San Jose, Calif.): Phycoerythrin-conjugated Leu-8 (PE-Leu-8, CD62L), PE-Leu-M5 (CD11c) fluorescein isothiocyanate (FITC) Leu 18 (CD45RA) and PE-Leu 18. The following conjugated monoclonal antibodies were obtained from Pharmingen (San Diego, Calif.): FITC-HIT3a (CD3), FITC-3G8 (CD16), biotin and PE-RPA-T8 (CD8), Cy5-PE "CYCHROME" conjugated RPA-T4 (CD4), FITC-Cl111 (CD11a), and Cy5-PE HI30 (CD45). When biotin-conjugated monoclonal antibodies were used, they were visualized with Cy-chrome conjugated avidin (Pharmingen). The glutathione stain does not affect the intensity nor the ability to detect any of the immunofluorescence reagents (Roederer, et al., 1993).

The following combinations of immunophenotype surface markers/chromophores were used in the child study (fluorescein (FITC), phycoerythrin (PE), and "CYCHROME" (Cy5-PE)): (1) CD16, CD11c, and CD45; (2) CD3, CD4, and CD8; (3) CD11a, CD45RA, and CD8; and (4) CD45RA, CD62L, and CD8.

The following antibody/chromophore combinations were used in the adult study: (1) FITC CD62L, PE CD45RA, and Cy5-PE CD8; (2) FITC CD62L, PE CD45RA, and Cy5-PE CD4; (3) FITC CD11a, PE CD45RA, and Cy5-PE CD4; (4) FITC CD11a, PE CD45RA, and Cy5-PE CD8; (5) FITC CD3, PE CD8, and Cy5-PE CD4; and (6) FITC CD14, PE CD16, and Cy5-PE CD45.

Concentrated antibody preparations were titered in combinations with unconjugated antibody to obtain saturating reagents that were on-scale in fluorescence. Enough reagent was premixed to study all the subjects in each respective study, ensuring comparable fluorescence distributions across all experiments within a study.

H. Multiparameter Flow Cytometry

General protocols for flow cytometric analysis and clinical data analysis for flow cytometry are detailed in Keren, et al. (1989) and Coon, et al. (1994).

Peripheral blood mononuclear cells (PBMC) were isolated from 3 ml (child study) or 6 ml (adult study) heparinized whole blood by Ficoll-Hypaque density centrifugation (Ficoll-Paque was obtained from Pharmacia, Uppsala, Sweden). The PBMC were washed and suspended in RPMI media deficient in biotin, phenol red, and riboflavin and stained for intracellular glutathione concentrations as previously described (Roederer, et al., 1993).

The PBMC were then washed and stained with the combinations of fluorochrome conjugated monoclonal antibodies listed above at 4° C. The stained PBMC were resuspended in 0.5% (adult study) or 0.8% (child study) paraformaldehyde in RPMI to inactivate HIV and analyzed on a dual laser (argon 360 nm, argon 488 nm) flow cytometer (FACStar Plus, Becton Dickinson) interfaced to a VAX 6300 computer (Digital Computer, Maynard, Mass.) and "FACS-DESK" software (Moore and Kautz, 1986). Independent analyses have shown that staining for intracellular glutathione does not affect subsequent staining for surface marker proteins, and fixing with paraformaldehyde alters neither the representation of subsets nor surface antigen quantitation.

For each cell, data for forward scatter, side scatter, and the fluorescences of fluorescein (515–545 nm bandpass filter), phycoerythrin (570–600 nm), and Cy5-PE (650–690 nm) were collected. For each stain, data from 50,000 cells were collected and analyzed by "FACS-DESK" software (Moore and Kautz, 1986). For subset frequencies, a lymphocyte gate was used. In addition, gates uniquely identifying CD4 or CD8 T cells and their subsets (e.g., as shown in FIGS. 1B, 1C and 1D) were applied.

In the adult study, absolute numbers of subsets of CD4 or CD8 T cells were found by multiplying their representation by the absolute subset counts. For instance, the number of naive CD4 per $\mu$l of whole blood was calculated by multiplying the fraction of CD4 T cells which were naive (from FACS gating) by the absolute CD4 count per $\mu$l of blood. CD4 and CD8 counts for the control (HIV uninfected) population were not obtained. of course, this calculation method can be used in any of the methods detailed herein, where it is desired to obtain absolute counts of a subpopulation of T-cells.

In the child study, total counts of all subsets of T cells were calculated as follows: (percentage of subset/percentage of lymphocytes)×absolute lymphocyte count. The percentage of CD4 and CD8 T cells was calculated from the percentage of $CD3^+CD4^+$ or $CD3^+CD8^+$ T cells (Table 1). The percentage of lymphocytes was calculated as the percentage of cells expressing the common leukocyte antigen (all isoforms of CD45), which are not monocytes ($CD11c^{hi}$) or contaminating granulocytes ($CD11c^{lo}$, $CD16^{hi}$). The absolute lymphocyte count was taken from the CBC. To define subsets, only $CD8^{hi}$ expression was used to identify CD8 T cells. To exclude natural killer (NK) cells (which are $CD8^{lo}$), a very bright reagent which segregates them from CD8 T cells was used.

I. Statistical Analyses—Child Study

Differences between HIV-negative control and HIV-infected children were evaluated by Mann-Whitney U non-parametric testing. Linear correlations between absolute counts (cells/$\mu$l) of lymphocyte subsets with each other were evaluated by least squares regression analysis. Frequency testing of groups of study subjects was done by chi-squared analysis. All statistical evaluations were performed with StatView 4.0 software (Abacus Concepts, Berkeley, Calif.) and an Apple Macintosh microcomputer (Apple Computer, Cupertino, Calif.). All p values are two-tailed.

J. Statistical Analyses—Adult Study

JMP for the Apple Macintosh (SAS Institute, Cary, N.C.) was used for analysis and display of statistical comparisons. Comparisons of distributions were performed by the non-parametric 2 sample Wilcoxon rank test. Other statistical analyses known to those skilled in the art may be employed as well.

EXAMPLE 1

T Cell Subset Phenotypes in Adults

Both CD4 and CD8 T cells from blood were subdivided into subsets based on surface phenotypes using a combination of CD62L (L-selectin) and CD45RA antibodies and a flow cytometer (as described above in Materials and Methods). Naive T cells belong to the subsets which stain brightly with both of these antibodies, and dimly for CD11a (LFA-1α) (Sanders, et al., 1988a; Picker, et al., 1993; Okumura, et al., 1993). Three other subsets of cells, consisting of the other combinations of CD62L and CD45RA expression, comprise the memory compartment (Picker, et al., 1993; Okumura, et al., 1993).

FIGS. 1A, 1B, 1C and 1D show the T cell subset phenotypes obtained from a PBMC sample from a healthy adult. The lymphocytes were selected by scatter gates (FIG. 1A). Within lymphocytes, CD4 and CD8 T cells were discriminated using CD4 and CD8 staining (FIG. 1B). Also evident are NK cells (dim CD8 staining) and B cells (negative for both CD4 and CD8).

Within both CD4 and CD8 cells are several subsets, detailed in FIGS. 1C and 1D. The naive subsets (black rectangular box) of both CD4 and CD8 lineages are defined as CD45RA+ and CD62L+; the remaining cells comprise the memory subsets (Mem). Within CD8 T cells (FIG. 1D) are at least 3 memory subsets: cells expressing only one of CD45RA or CD62L, and those expressing neither. Within CD4 T cells (FIG. 1C) are two major memory subsets: both are CD4SRA-, but one is CD62L+ and the other is CD62L-. In healthy adults, there are very few CD4 T cells with the CD45RA+ CD62L- phenotype (averaging 5% of total CD4). However, in HIV-infected adults, this population becomes much more prevalent (averaging 15% of all CD4 and as much as 40–50% in some patients; see FIG. 4B for an example).

Naive CD4 T cells differ from naive CD8 T cells in that the CD45RA expression on CD8 T cells is uniformly higher than on CD4 T cells. Indeed, even the CD45RA "negative" CD8 cells still display low levels of CD45RA. Since some of these cells express as much CD45RA as CD4 naive cells, the frequencies of naive cells of each lineage must be determined independently (i.e., using CD3 to identify T cells—it is not possible to use a "gate" based on CD45RA and CD62L expression that includes all CD8 and CD4 naive T cells and excludes memory T cells). Thus, enumerating CD8 and CD4 naive T cells in PBMC samples requires simultaneous FACS measurement of three cell surface antigens in two separate tubes, i.e., CD8 (or CD4), together with CD45RA and CD62L.

The above-described experiments, particularly data in FIGS. 1A and 1B, demonstrate an exemplary way of sorting a sample of peripheral blood mononuclear cells (PBMC) isolated from either normal or immunocompromised (e.g., HIV-infected) subjects into sets (e.g., a CD4 set and a CD8 set) of T-cell types. The example demonstrates how one can determine the ratio of naive cells relative to the total number of cells (naive:total) in each set. In this case, such determining is achieved by detecting immunoreactivity of T-cells in the CD4 (FIG. 1C) and CD8 (FIG. 1D) sets with two antibodies (CD45RA and CD62L) selectively reactive with naive T-cell surface proteins. As stated above, similar results may be achieved by employing (anti-) CD4 or CD8 antibodies in combination with CD45RA and CD11a antibodies (in place of the CD45RA and CD62L antibodies). In this case, naive cells are identified by bright staining for CD45RA and "dim", or low levels of staining for CD11a.

EXAMPLE 2

Multiparameter FACS Analysis of CD8 T cells from Children

CD8 T cells isolated from children were analyzed by multiparameter FACS analysis. Representative CD8 T cell subsets, in the form of 5% probability contour plots of CD8 T cells from a healthy adult, two HIV-negative control children, and two HIV-infected children, are shown in FIGS. 2A–J. The solid arrow points to the naive subset, which is $CD11a^{lo}$, $CD45RA^{hi}$, as well as $CD62L^{hi}$ (FIGS. 2B, 2D, 2F, 2H and 2J, solid arrow). There are three subsets of memory CD8 T cells, all of which are $CD11a^{hi}$ (FIGS. 2A, 2C, 2E, 2G and 2I). These memory subsets can be distinguished from each other according to CD45RA and CD62L expression (FIGS. 2B, 2D, 2F, 2H and 2J).

The memory subset with the highest frequency is $CD45RA^-$, $CD62L^-$. The CD8 T cells of HIV-negative children (FIGS. 2C, 2D, 2E and 2F) are virtually all naive. The frequency of the naive subset is substantially decreased in HIV-infected children (FIGS. 2G, 2H, 2I and 2J) and conversely, the frequency of all memory subsets are increased. Although the percentage of naive CD8 T cells is decreased, the phenotype of the remaining cells is unchanged. Note that PE-conjugated CD45RA was used in FIGS. 2A, 2C, 2E, 2G and 2I, while FITC-conjugated CD45RA was used in 2B, 2D, 2F, 2H and 2J, accounting for the apparent difference in staining intensity.

Flow cytometric analysis for three surface markers identified a subset of cells which expressed low levels of CD11a ($CD11a^{lo}$) and high levels of CD45RA ($CD45RA^{hi}$, FIGS. 2A, 2C, 2E, 2G and 2I, solid arrow). A similar analysis identified a subset which was $CD45RA^{hi}$ and $CD62L^{hi}$ (FIGS. 2B, 2D, 2F, 2H and 2J, solid arrow). This subset fits previous definitions of the naive subset of CD8 T cells (Picker, et al., 1993; Okumura, et al., 1993a).

Additional experiments performed in support of the present invention demonstrated, using four-color immunofluorescence analysis, that all cells that fit the naive phenotype ($CD11a^{lo}$, $CD45RA^{hi}$) were also $CD62L^{hi}$, but that not all $CD11a^{lo}$ cells were $CD45RA^{hi}$. Accordingly, it is preferable to simultaneously measure three antigens (e.g., CD8, CD45RA, and CD11a or CD62L) in order to uniquely identify the naive cells.

In addition to the naive subset, FIGS. 2A and 2B show three other subsets of CD8 T cells, which are referred to herein as memory cells because they are all $CD11a^{hi}$ (Sanders, et al., 1988a). These subsets of memory or effector cells further segregated on the basis of CD45RA and CD62L expression (FIGS. 2B, 2D, 2F, 2H and 2J). In general, the most frequent of these was the $CD45RA^-$, $CD62L^-$ subset (hollow arrow); additional memory subsets expressed only CD62L or only CD45RA.

EXAMPLE 3

Multiparameter FACS Analysis of CD8 T Cells from Adults

FIGS. 3A, 3B, 3C, 3D, 3E, 3F, 3G and 3H are examples of CD8 T cell subsets in healthy (FIGS. 3E–H) and HIV-infected (FIGS. 3A–D) adults. Four examples each from the HIV-negative cohort (FIGS. 3E–H) and the HIV+ cohort (FIGS. 3A–D) were selected to show the range of naive T cell representation in these groups, and are arranged in order of increasing naive CD8 T cell representation (left to right). Only CD8 T cells are shown (based on gating similar to that shown in FIGS. 1A–D).

The loss of the naive subset in the infected individuals is seen by the decrease of the CD45RA+ CD62L+ subset, and a corresponding increase in the memory subset. Note that an increase of memory cells in one HIV+ adult may reflect expansion of a different subset than in another HIV+ adult (e.g., compare FIGS. 3C and 3D). While there is a marked variation in the representation of the various subsets within individuals (both HIV-infected and uninfected), the phenotypes of these subsets are constant.

Figure 4B:
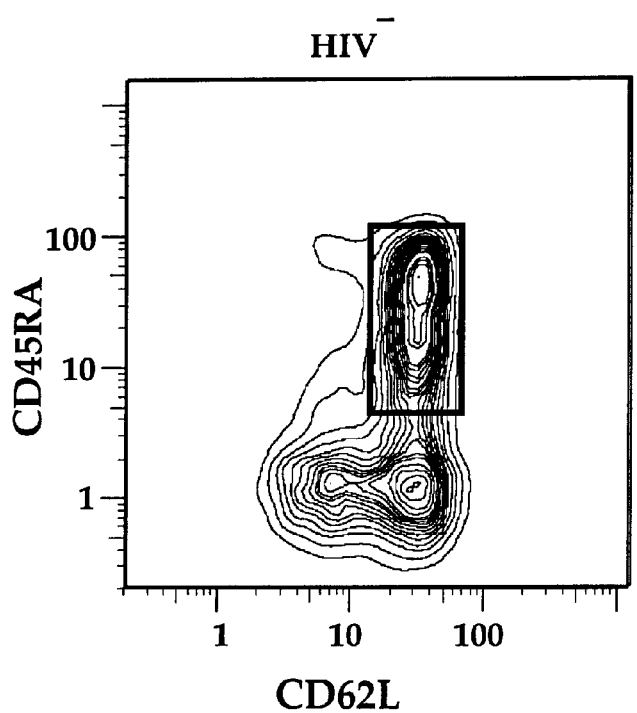

FIGS. 4A and 4B show examples of CD4 T cell subsets in an uninfected adult (FIG. 4B) and an HIV-infected adult (FIG. 4A), with the box denoting the position of the naive cells. This HIV-infected adult has a large proportion of CD45RA+ CD4 T cells, but note that these are not naive T cells, since they have at least two characteristics distinguishing them as memory cells: (i) they are considerably brighter for CD45RA than naive CD4 cells, and (ii) they are low for CD62L expression. Furthermore, they express HLA-DR and CD38 activation markers and contain very low intracellular glutathione.

The data described above demonstrate that HIV-infected adults lose a significant fraction of naive T cells of both CD4 (FIGS. 4A and 4B) and CD8 (FIGS. 3A–H) lineages. This loss is visible as a decrease in the representation of the CD45RA+ CD62L+ cells. Absolute counts (cells per $\mu$l of blood) of these subsets, calculated by combining these FACS frequency data with CBC data, show a similar decline (see below). All of the HIV+ individuals shown had very few naive cells. Even so, the individual from whom data are shown in FIG. 3C had a considerable fraction of memory CD62L+ cells, while the one from whom data are shown in FIG. 3D had a considerable fraction of memory CD45RA+ cells. Measurement of only one or the other marker would therefore not have revealed the naive cell loss in these individuals.

EXAMPLE 4

Functional Analysis of CD8 Subsets from Children

To confirm the previously identified functional differences between naive and memory CD8 subsets, three types of analyses were performed in the child study: cytoplasmic calcium flux (a prerequisite event for proliferation, with the extent of the flux being related to proliferative capacity); proliferative response to several mitogenic stimuli, measured by DNA synthesis; and cytokine mRNA profiles in response to several stimuli, determined by reverse polymerase chain reaction (PCR; Mullis, 1987a; Mullis, et al., 1987b).

The experiments shown in FIGS. 5A–E and 6 using adult cells were performed on PBMC isolated from buffy coats of HIV-negative healthy adults. The cells were stained at room temperature with fluorescent conjugates of CD8, CD45RA, and CD62L for 15 minutes in the presence of 0.02% sodium azide, and washed extensively with azide-free medium. These conditions were employed because they did not alter the ability to flux calcium or stimulate the cells.

FIGS. 5A–E show that the different subsets have substantially different capacities to transport calcium in response to the CD3 triggering. The T-cell subsets shown in the FIGS. 5A–E are as defined in FIGS. 2A–J. The data show that the ability of the different subsets to flux calcium after CD3 stimulation is markedly different. While the kinetics are roughly equivalent (influx began approximately 45 sec after stimulation), the extent of the flux and the resulting quasi-equilibrium concentration of calcium were markedly higher in the naive cells. The CD45RA+ CD62L− memory subset had at best a nominal calcium flux.

Each point represents the average value for 10 seconds of data (approximately 200 cells/sec for the naive subset; as low as 30 cells/sec for the rarest memory population). The data points for the naive are mostly hidden under the curve. The four curves are reproduced in the right panel for comparison. The naive cells responded well, with a vigorous and sustained increase in cytoplasmic calcium. In contrast, the memory subsets showed a much weaker flux.

The ability to flux calcium was correlated with the subsequent mitogenic capacity of these cells (Table 2, below); i.e., the naive cells proliferated to a greater extent than the memory subsets.

TABLE 2

PROLIFERATIVE CAPACITY OF CD8 NAIVE AND MEMORY SUBSETS

| Stimulus | Naive (cpm)[1] | CD45RA CD62L− (cpm)[1] | (fold)[2] | CD45RA CD62L+ (cpm)[1] | (fold)[2] |
|---|---|---|---|---|---|
| Unstimulated | 17 | nd | | 10 | |
| Leu4 + PMA | 1600 | 640 | 2.4 | 650 | 2.5 |
| Leu4 + B7 | 5050 | 2010 | 0.8 | 6500 | 2.5 |
| SEA | 140 | 39 | 8.7 | 24 | 4.9 |
| SEA + PMA | 690 | 300 | 1.8 | 390 | 2.4 |

[1]Means counts per minute for triplicate wells (5,000 cells per V-bottom well; 4-d stimulation). Standard deviations were all <15% of the mean.
[2]The ratio of the proliferation signal for the naive cells to the proliferation signal for the memory population (background was subtracted from each value before division).

Figure 6:
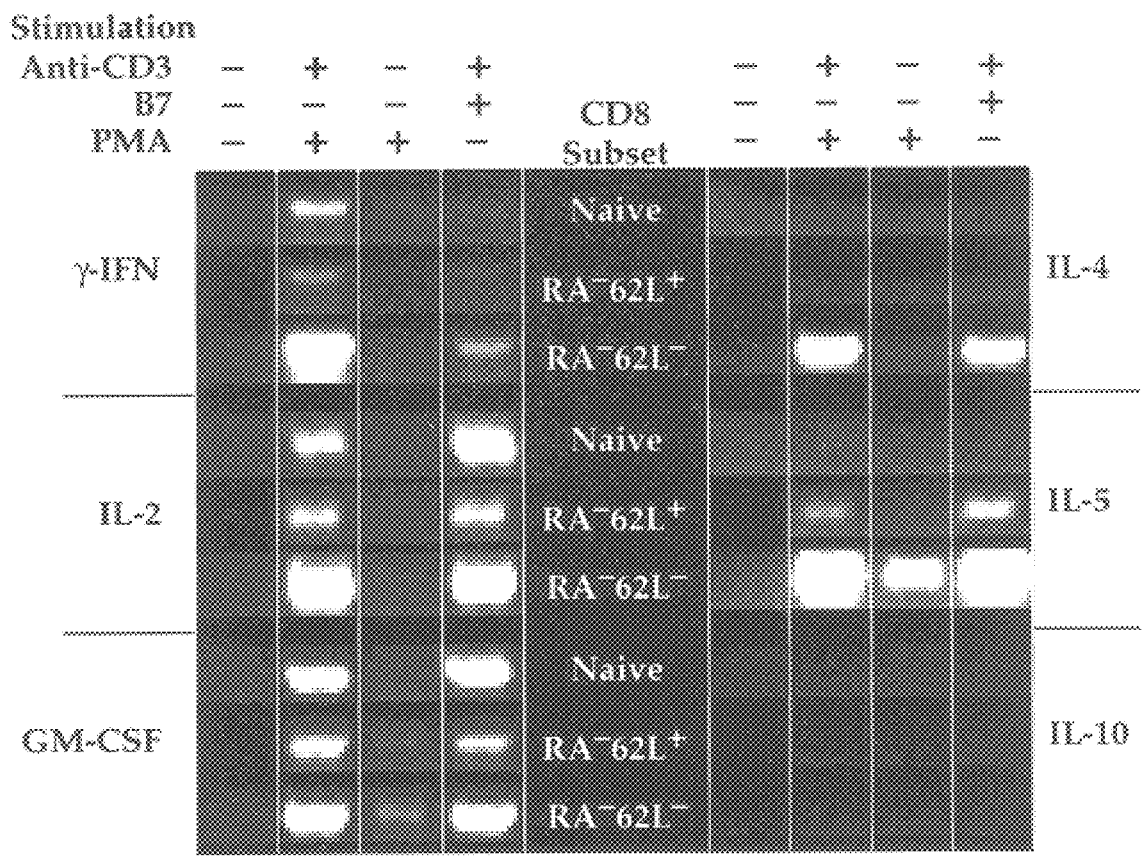
FIG. 6 shows a survey of cytokine messages made by three of the subsets in response to stimulation. This figure was generated from data obtained in the child study.

FIG. 6 shows a survey of cytokine messages made by three of the subsets in response to stimulation. Cells from the CD8 subsets were physically sorted to purity and cultured for 6 hours with various stimulants (indicated). Cytokine expression was then assessed by reverse PCR (Mullis, 1987a; Mullis, et al., 1987b). The naive cells did not express message for interleukin-4 (IL-4) or interleukin-5 (IL-5), and expressed only very low levels of γ-interferon (γ-IFN). None of the CD8 subsets made detectable interleukin-10 (IL-10).

Data from a limited survey of the cytokine profiles of the subsets (FIG. 6) are consistent with the known phenotype of naive and memory cells; i.e., naive cells had a more restricted cytokine profile and only the memory subsets made the typical memory/effector cytokines IL-4, IL-5, and γ-IFN.

EXAMPLE 5

Loss of Naive CD8 and Increase in Memory CD8 T Cells in Children

Data shown in FIGS. 2C–F demonstrate that the majority of the CD8 T cells in HIV-negative control children are naive (solid arrows). In contrast, the representative plots of HIV-infected children (FIGS. 2G–J) demonstrate a decrease of the naive subset and a commensurate increase of the memory subsets of CD8 T cells.

Summary data for all the children in the study are presented in FIGS. 7A–F, which show a distribution of CD8 T cell subsets among HIV-negative control and HIV-infected children. Since CD45RA alone is insufficient to distinguish naive from memory cells, there was no statistically significant difference ($p \leq 0.07$) in the numbers of cells defined only on the basis of this marker (FIGS. 7C and 7D). However, there was a very large difference ($p \leq 0.003$) when the naive cells were uniquely identified on the basis of three markers (FIGS. 7E and 7F).

The total CD8 T cell count (McGrath, 1990; Steihm and Wara, 1991) and the frequency of the CD45RA$^{hi}$, CD8 T cells (previously taken as the naive subset) did not differ significantly (Prince, et al., 1990; Giorgi and Detels, 1989; Teitel, et al., 1989) between the HIV-infected and control children. In contrast, the naive subset as defined herein (CD45RA$^{hi}$, CD11a$^{lo}$, CD62L$^{hi}$) was clearly decreased in HIV-infected children in absolute number ($p \leq 0.003$), as well as percentage of total CD8 T cells. While all memory subsets increased, the most significant increase was found for the CD45RA$^-$CD62L$^-$ subset ($p \leq 0.0004$). The other memory subsets are also increased, although not to the same extent (HIV-infected vs. HIV-negative controls, $p \leq 0.05$ for both subsets). Therefore, the increase in the total CD8 counts in HIV-infected children was due essentially only to an expansion of the memory subsets of CD8 T cells.

No differences were found for a variety of other variables. Within the group of HIV-infected children, no differences were observed between those who acquired HIV horizontally or vertically, or between those with or without AIDS. Similarly, among the HIV-negative controls, there were no differences between those who were or were not receiving growth hormone or L-thyroxine. In addition, no correlation was found between age and the number or percentage of naive CD8 T cells in either the HIV-negative or the HIV-infected children. Furthermore, no correlation was observed between disease severity and either CD4 or CD8 counts.

EXAMPLE 6

Loss of Naive CD8 and Increase in Memory CD8 T Cells in Adults

FIGS. 8A, 8B, 8C and 8D show representations of naive T cells within the CD4 and CD8 lineages from adults. In both lineages, there was a substantial decrease in the representation of naive T cells, and a corresponding increase in memory cells. This is more dramatic in CD8 T cells (FIGS. 8A and 8B) than CD4 T cells (FIGS. 8C and 8D): 90% of HIV-infected adults (FIG. 8A) had a lower fraction of naive CD8's than almost all uninfected adults (FIG. 8B). Fifty percent of CD8 T cells in healthy adults typically belonged to the naive subset; however, in most HIV-infected adults, less than 15 percent of CD8 cells were naive.

The decrease in the CD4 naive T cells may be even greater than these data show, due to the overlap in expression of CD45RA on memory CD4 T cells and naive CD4 T cells (e.g., see FIGS. 4A and 4B). This overlap results in an over-estimate of naive CD4 representation for infected adults. Although these data were calculated from the frequencies of CD62L+, CD45RA+ T cells, virtually identical results were obtained for each subject by determining the frequency of the CD11a-dim, CD45RA+ cells of both CD4 and CD8 T subsets.

The change in naive/memory representation did not necessarily reflect a decrease in the absolute numbers of the naive cells. For example, among the HIV-infected individuals with the highest CD4 counts, absolute naive CD8 counts were sometimes in the normal range, but significant elevation of the memory count resulted in the ratio of naive-:memory being well below the normal ratio of about one-half. The ratios are discussed in more detail in Example 8, below.

The experiments described in this example, and in Example 2, demonstrate one way of identifying an abnormal T-cell profile in an immunocompromised (e.g., HIV-infected) subject, namely, by comparing the naive:total ratios of CD4 or CD8 cells from the immunocompromised subject with the naive:total ratios of CD4 or CD8 cells from a non-immunocompromised subject. With reference to the present example, the data shown in FIGS. 8A–8D show distributions of the naive:total ratios for both CD8 (FIGS. 8A and 8B) and CD4 (FIGS. 8C and 8D) from immunocompromised (FIGS. 8A and 8C) and non-immunocompromised (FIGS. 8B and 8D) subjects.

It can be appreciated that in determining whether a particular individual's T-cell profile is normal or abnormal, the individual's naive:total CD4 and CD8 ratios may be compared to the means of the distributions illustrated in FIGS. 8A–8D. Standard clinical methodology may be employed to establish ranges for naive:total ratios that considered "normal" vs. "abnormal". These ranges will depend to some extent on the particular type of immunodeficiency under consideration. For example, in the present case (HIV-infected individuals), a suitable cut-off to distinguish "normal" from "abnormal" T-cell profiles based on the naive:total ratio of CD8 cells may be about 0.3. As seen from the above data, a ratio of less than about 0.3 indicates a preferential loss of naive T-cells in an HIV-infected (immunocompromised) subject.

Further, it will be understood that in the case of subjects being monitored over an extended period of time, or before and after a treatment, such as immunotherapy), it may be advantageous to compare the naive:total ratios of that subject's T-cells over time in order to establish any trends in the subject's T-cell profile which may provide a measure of the condition of the subject's immune system.

EXAMPLE 7

Figure 9A:
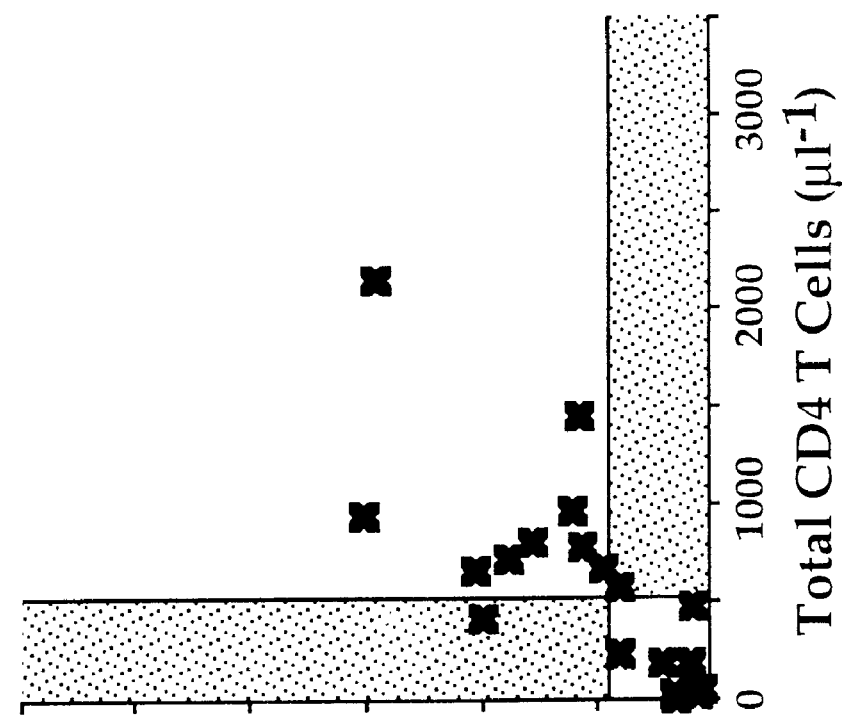
FIGS. 9A and 9B show total CD4 T cell and naive CD8 T cell counts in HIV-negative control (FIG. 9A) and HIV-infected (FIG. 9B) children. These figures were generated from data obtained in the child study.
Figure 9B:
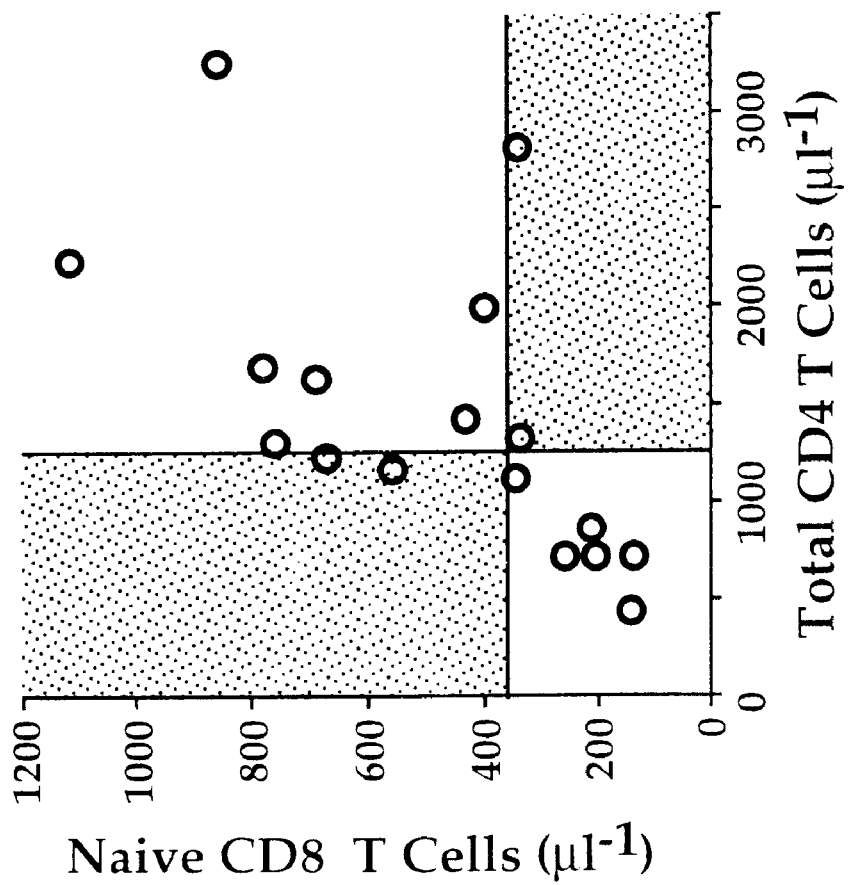

The Naive CD8 T Cell Count Correlates with the Total CD4 Count in HIV-Infected Children FIGS. 9A and 9B show that the naive CD8 and total CD4 counts are correlated in both HIV-negative (FIG. 9A) and HIV-infected (FIG. 9B) children. The lines segregate the groups of children into quadrants according to median total CD4 T cell counts and naive CD8 T cell counts within each group. Of the 19 HIV-infected children, nine are above the medians for both CD4 and naive CD8 T cell counts, and eight are below both medians. Of the 17 control children, seven are above, and six are below both of their respective medians. The correlation of CD4 and naive CD8 T cell counts among HIV-negative children bordered on significance (chi-square, $p \leq 0.06$); for HIV-infected children, it was highly significant ($p < 0.001$).

All but one of the HIV-infected children whose naive CD8 T cell counts fell below their median (186 cells/$\mu$l) had CD4 T cell counts that also fell below their median (526 cells/$\mu$l). Similarly, all but one of the HIV-infected children with high CD4 counts had high naive CD8 T cell counts. This correlation was significant by chi-square analysis and Fisher's exact test ($p \leq 0.001$).

The specific clustering of CD4 counts and naive T cell counts in the HIV-infected children was also visible in a regression analysis of the data discussed above. A least squares linear analysis computed for the data demonstrated that CD4 T cell counts correlated better with naive CD8 T cell counts in HIV-infected children than in HIV-negative children ($r^2$ for HIV-negative control, 0.38; for HIV-infected, 0.54).

Total CD8 T cell counts, in contrast, showed essentially no correlation with CD4 counts either in HIV-negative or in HIV-infected children. That is, there was no significant correlation of total CD4 and CD8 counts as measured by chi-square analysis of HIV-infected children above and below the medians for CD4 and CD8 T cells ($p \leq 0.07$); and there was less correlation by linear regression analysis ($r^2$ for HIV-negative control, 0.42; for HIV-infected, 0.29).

FIG. 10C shows the absolute number of naive CD4 T cells. The shaded area is the interquartile range; the line connecting medians is not drawn. If naive and memory CD4 T cells were lost from HIV-infected individuals at the same rate, then the shaded region would be centered on the dashed line. (The slope of the dashed line, 0.5, is the fraction of CD4 T cells which are naive in uninfected adults; see Table 3.) Since the distribution actually curves well below this line, naive CD4 T cells were lost preferentially to memory CD4 T cells in HIV-infected individuals.

TABLE 3

REPRESENTATION OF CD4 AND CD8 T CELLS IN WHOLE BLOOD[1]

| Cells | HIV+ (CD4/μl)[2] 0–200 | 200–500 | >500 | HIV−[2] |
|---|---|---|---|---|
| | Fraction of T Cells that are Naive (%) | | | |
| CD8 | 12 (7–18) | 16 (11–24) | 23 (16–33) | 52 (41–59) |
| CD4 | 27 (18–37) | 39 (30–49) | 45 (30–57) | 50 (41–58) |
| | Absolute Number of Cells/μl of Blood | | | |
| Total CD8 | 520 (310–780) | 790 (580–1110) | 750 (590–1100) | 620 (330–910)[3] |
| Naive CD8 | 58 (34–94) | 120 (93–160) | 175 (140–230) | 320[4] |
| Naive CD4 | 18 (7–37) | 120 (85–178) | 250 (160–230) | 489[5] |

[1]Numbers presented are the median values for each group (either percent of each lineage that is naive in the upper portion of the table, or cells/μl for each subset in the lower portion). The interquartile range is given in parentheses.
[2]Number of individuals in each group: HIV− = 44; HIV+, 0–200 = 109; 200–500 =0 105; >500 = 28.
[3]This is the value for all HIV− adults seen at the same clinic which performed our absolute counts, including subjects not in our cohort.
[4]This value is based on the total CD8 count (620) multiplied by the average percent of CD8 T cells which are naive in uninfected adults from our study (52%).
[5]The average value for total CD4 count (978), for all HIV adults seen at the clinic, multiplied by the fraction of CD4 T cells which are naive (50%).

EXAMPLE 8

The Naive T Cell Count Correlates with the Total CD4 Count in HIV-Infected Adults FIGS. 10A, 10B and 10C show plots of the correlation of naive T cell representation with absolute CD4 count. The data indicate that naive cells in both CD8 and CD4 lineages were lost preferentially during the progression of HIV disease.

In FIG. 10A, the absolute number of naive CD8 T cells is plotted against the absolute total CD4 count. Each dot represents one individual. The line connects the median values for individuals grouped by CD4 counts (each group is based on a range of 100 CD4 cells/μl). The shaded area is the interquartile range for the groups. The range for uninfected adults is from Table 3.

FIG. 10B shows the total CD8 counts plotted as in FIG. 10A. Most infected adults had more total CD8 cells than uninfected adults. Since the number of naive T cells declines during the progression of AIDS, the increase was due to the expansion of memory CD8 T cells.

In general, as total CD4 counts fell, naive CD8 T cell counts also fell (FIG. 10A). Since the absolute number of CD4 T cells per μl of blood provides a reasonable indication (surrogate marker) for the progression of AIDS, these data were interpreted as indicating that the naive CD8 T cells were selectively lost during the progression of AIDS. While there is a loose correlation between these two counts, it is also apparent than many individuals have either considerably more, and others fewer, naive CD8 T cells than would be predicted by their total CD4 count. Therefore, the naive CD8 T cell count may provide a useful marker to distinguish individuals who are very different immunologically and yet would be stratified together by the use of CD4 counts.

Naive CD4 T cells are also preferentially lost during HIV disease progression (FIG. 10C). While more than half of CD4 T cells in healthy adults were in the naive subset, about one-fourth were naive in HIV-infected adults with CD4 counts under 200/μl (Table 3). Since the preferential loss of naive CD4 T cells aralleled the loss of naive CD8 T cells, a similar mechanism might account for the decrease in both naive subsets.

While the invention has been described with reference to specific methods and embodiments, it is appreciated that various modifications and changes may be made without departing from the invention.

It is claimed:

1. A method of measuring the T-cell profile of an immunocompromised subject relative to the T-cell profile of a non-immunocompromised subject, comprising sorting a sample containing peripheral blood mononuclear cells (PBMC) obtained from said immunocompromised subject into one or more sets of T-cells types selected from the group consisting of CD4+, CD8+, and CD4+ plus CD8+, determining in each set the ratio of naive cells relative to the total number of cells (naive:total) by detecting immunoreactivity of T-cells in each set with at least two different antibodies selectively reactive with T-cell surface proteins, said antibodies comprising
  a) a first antibody selectively reactive with a CD45RA T-cell surface protein, and
  b) a second antibody selectively reactive with either a CD62L or a CD11a T-cell surface protein, and comparing the naive:(otal ratios of sets from said immunocompromised subject with the naive:total ratios of analogous sets from a non-immunocompromised subject.

2. The method of claim 1, wherein the T-cell profile of the immunocompromised subject includes the preferential loss of naive T-cells in the immunocompromised subject.

3. The method of claim 1 applied to an HIV-infected subject.

4. The method of claim 1 applied to a subject undergoing immunotherapy.

5. The method of claim 1, wherein said determining is accomplished using a fluorescence-activated cell sorter (FACS) and three-color immunophenotyping.

6. The method of claim 1, wherein said first antibody is anti-CD45RA and said second antibody is anti-CD62L.

7. The method of claim 1, wherein said first antibody is anti-CD45RA and said second antibody is anti-CD11a.

8. A method of evaluating the efficacy of a drug to stimulate the production of naive T cells in a subject, comprising obtaining a first sample containing peripheral blood mononuclear cells (PBMC) from said subject, administering a suitable dose of said drug to said subject, obtaining a second sample containing peripheral blood mononuclear cells (PBMC) from said subject, isolating from said first and second samples, first and second populations of T cells, respectively, determining the number of naive T cells in each population, said determining including the detection of immunoreactivity of T-cells in the populations with at least two different antibodies selectively reactive with T-cell surface proteins, said antibodies comprising
  a) a first antibody selectively reactive with a CD45RA T-cell surface protein, and
  b) a second antibody selectively reactive with either a CD62L or a CD11a T-cell surface protein, and
  identifying the drug as effective if the number of naive T-cells in the second population is significantly greater than the number of naive T-cells in the first population.

9. The method of claim 8, wherein said isolating includes sorting each population into one or more sets of T-cell types selected from the group consisting of CD4+, CD8+, and CD4+ plus CD8+, and said determining includes determining the number of naive T cells in each set of each population.

10. The method of claim 8, wherein said first antibody is anti-CD45RA and said second antibody is anti-CD62L.

11. The method of claim 8, wherein said first antibody is anti-CD45RA and said second antibody is anti-CD11a.

* * * * *